(12) United States Patent
Kansal et al.

(10) Patent No.: US 7,923,575 B2
(45) Date of Patent: Apr. 12, 2011

(54) ASYMMETRIC SYNTHESIS OF (S)-(+)-3-(AMINOMETHYL)-5-METHYLHEXANOIC ACID

(75) Inventors: Vinod Kumar Kansal, Haryana (IN); Brijnath P. Chaurasia, Uttar Pradesh (IN); V. Govardhan Rao, Andhra Pradesh (IN); Anand Prakash Tiwari, Uttar Pradesh (IN)

(73) Assignee: Teva Pharmaceutical Industries Limited, Petah Tiqva (IL)

( * ) Notice: Subject to any disclaimer, the term of this patent is extended or adjusted under 35 U.S.C. 154(b) by 0 days.

(21) Appl. No.: 12/589,175

(22) Filed: Oct. 19, 2009

(65) Prior Publication Data

US 2010/0081841 A1 Apr. 1, 2010

Related U.S. Application Data

(62) Division of application No. 12/290,286, filed on Oct. 28, 2008, now Pat. No. 7,851,651, which is a division of application No. 11/523,876, filed on Sep. 19, 2006, now Pat. No. 7,446,220.

(60) Provisional application No. 60/718,689, filed on Sep. 19, 2005, provisional application No. 60/754,392, filed on Dec. 27, 2005, provisional application No. 60/763,593, filed on Jan. 30, 2006, provisional application No. 60/752,434, filed on Dec. 20, 2005, provisional application No. 60/753,220, filed on Dec. 21, 2005, provisional application No. 60/763,696, filed on Jan. 30, 2006, provisional application No. 60/839,947, filed on Aug. 23, 2006.

(51) Int. Cl.
*C07C 205/00* (2006.01)

(52) U.S. Cl. ........................................... 562/553
(58) Field of Classification Search ................... None
See application file for complete search history.

(56) References Cited

U.S. PATENT DOCUMENTS

| | | |
|---|---|---|
| 5,010,189 A | 4/1991 | Herold et al. |
| 5,599,973 A | 2/1997 | Silverman et al. |
| 5,616,793 A * | 4/1997 | Huckabee et al. ............ 562/553 |
| 5,629,447 A | 5/1997 | Huckabee et al. |
| 5,637,737 A | 6/1997 | Andres et al. |
| 5,637,767 A | 6/1997 | Grote et al. |
| 6,001,876 A | 12/1999 | Singh |
| 6,187,930 B1 | 2/2001 | Torrens-Jover et al. |
| 6,197,819 B1 | 3/2001 | Silverman et al. |
| 6,333,198 B1 | 12/2001 | Edmeades et al. |
| 6,359,169 B1 | 3/2002 | Silverman et al. |
| 6,488,964 B2 | 12/2002 | Bruna et al. |
| 6,580,003 B2 | 6/2003 | Deng et al. |

(Continued)

FOREIGN PATENT DOCUMENTS

CN 1 634 869 7/2005

(Continued)

OTHER PUBLICATIONS

Andruszkiewicz and Silverman, "A convenient synthesis of 3-Alkyl-4-aminobutanoic acids", Synthesis, pp. 953-955 (1989).

(Continued)

*Primary Examiner* — Karl J Puttlitz
(74) *Attorney, Agent, or Firm* — Kenyon & Kenyon LLP

(57) ABSTRACT

The invention encompasses processes for the synthesis of (S)-(+)-3-(aminomethyl)-5-methylhexanoic acid, (S)-Pregabalin, and intermediates of (S)-Pregabalin.

32 Claims, 4 Drawing Sheets

U.S. PATENT DOCUMENTS

| | | | |
|---|---|---|---|
| 6,642,398 B2 | 11/2003 | Belliotti et al. | |
| 6,797,730 B2 | 9/2004 | Xiang et al. | |
| 6,833,458 B2 | 12/2004 | Liu et al. | |
| 6,891,059 B2 | 5/2005 | Burk et al. | |
| 6,924,377 B2 | 8/2005 | Blazecka et al. | |
| 6,927,036 B2 | 8/2005 | Gallop et al. | |
| 6,942,876 B2 | 9/2005 | Magnus-Miller et al. | |
| 7,022,678 B2 | 4/2006 | Hurley et al. | |
| 7,141,695 B2 | 11/2006 | Przewosny et al. | |
| 7,446,220 B2 | 11/2008 | Kansal et al. | |
| 7,462,738 B2 | 12/2008 | Hedvati et al. | |
| 2001/0016665 A1 | 8/2001 | Grote et al. | |
| 2002/0012679 A1 | 1/2002 | Bruna et al. | |
| 2003/0212290 A1 | 11/2003 | Burk et al. | |
| 2003/0225149 A1 | 12/2003 | Blazecka et al. | |
| 2005/0070483 A1 | 3/2005 | Donevan et al. | |
| 2005/0222464 A1 | 10/2005 | Hoge, II | |
| 2005/0228190 A1 | 10/2005 | Bao et al. | |
| 2005/0250818 A1 | 11/2005 | Koike et al. | |
| 2005/0267170 A1 | 12/2005 | Koike et al. | |
| 2005/0283023 A1 | 12/2005 | Hu et al. | |
| 2006/0128765 A1 | 6/2006 | Wood et al. | |
| 2006/0183791 A1 | 8/2006 | Khanzhin et al. | |
| 2006/0270871 A1 | 11/2006 | Khanduri et al. | |
| 2007/0073085 A1 | 3/2007 | Hedvati et al. | |
| 2007/0135356 A1 | 6/2007 | Scheuerman et al. | |
| 2007/0191636 A1 | 8/2007 | Kansal et al. | |
| 2007/0197827 A1 | 8/2007 | Kansal et al. | |
| 2008/0014280 A1 | 1/2008 | Kumar et al. | |
| 2008/0311635 A1 | 12/2008 | Riva et al. | |
| 2009/0143615 A1 | 6/2009 | Allegrini et al. | |

FOREIGN PATENT DOCUMENTS

| | | |
|---|---|---|
| CZ | 297 970 | 3/2007 |
| EP | 1 992 609 | 11/2008 |
| EP | 2 067 768 | 6/2009 |
| WO | WO 96/38405 | 12/1996 |
| WO | WO 96/38405 A | 12/1996 |
| WO | WO 96/40617 | 12/1996 |
| WO | WO 96/40617 A1 | 12/1996 |
| WO | WO 01/55090 | 8/2001 |
| WO | WO 01/55090 A1 | 8/2001 |
| WO | WO 2003/020273 | 3/2003 |
| WO | WO 2006/000904 | 1/2005 |
| WO | WO 2005/100580 | 10/2005 |
| WO | WO 2006/000904 | 1/2006 |
| WO | WO 2006/008640 | 1/2006 |
| WO | WO 2006/110783 | 10/2006 |
| WO | WO 2006/121557 | 11/2006 |
| WO | WO 2006/122255 | 11/2006 |
| WO | WO 2006/122258 | 11/2006 |
| WO | WO 2006/136087 | 12/2006 |
| WO | WO 2007/035789 | 3/2007 |
| WO | WO 2007/035890 | 3/2007 |
| WO | WO 2007/100086 | 9/2007 |
| WO | WO 2007/139933 | 12/2007 |
| WO | WO 2007/143113 | 12/2007 |
| WO | WO 2008/004044 | 1/2008 |
| WO | WO 2008/007145 | 1/2008 |
| WO | WO 2008/009897 | 1/2008 |
| WO | WO 2008/040935 | 4/2008 |
| WO | WO 2008/062460 | 5/2008 |
| WO | WO 2008/118427 | 10/2008 |
| WO | WO 2009/010554 | 1/2009 |

OTHER PUBLICATIONS

Burk et al., "An Enantioselective Synthesis of (S)-(+)-3-Aminomethyl-5-methylhexanoic Acid via Asymmetric Hydrogenation", J. Org. Chem., 68(14): 5731-5734 (2003).

Hoekstra et al., "Chemical Development of Cl-1008, an Enantiomerically Pure Anticonvulsant," Organic Process Research and Development, 1(1): 26-38 (1997).

Liu et al., "Asymmetric syntheses of trans-3,4-disubstituted 2-piperidinones and piperidines," Tetrahedron: Asymmetry, 12:419-426 (2001).

Lin et al., "Chiral HPLC Separations for Process Development of S-(+)-Isobutyl GABA, A Potential Anti-Epileptic Agent", J. Liq. Chrom. & Rel. Technol., 19(16), 2699-2708 (1996).

Martin, L. et al., "Pregabalin," Drugs of the Future, 24(8): 862-870 (1999).

Serfass et al., "General Synthesis of 3-Substitued Alkenyl GABA as Potential Anticonvulsants," Bioorganic & Medicinal Chemistry Letters 8 (1998) 2599-2602.

Yuen et al., "Enantioselective Synthesis of PD144723: A Potent Stereospecific Anticonvulsant", Bioorganic & Medicinal Chemistry Letters, 4(6), 823-826(1994).

US Office Action, dated Oct. 25, 2007, from related U.S. Appl. No. 11/523,865, filed Sep. 19, 2006.

Andruszkiewicz et al., "A Convenient Synthesis of 3-Alkyl-4-Aminobutanoic Acids", Synthesis, pp. 953-955 (1989).

Barnes et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram", J. Am.Chem.Soc., vol. 124, No. 44, pp. 13097-13105 (2002).

Berner et al.,"Asymmetric Michael Additions to Nitroalkenes," European Journal of Organic Chemistry, 1877-1894 (2002).

Boots et al., "Hypocholesterolemic Agents VII: Inhibition of β-Hydroxy-β-methylglutaryl-CoA Reductase by Monoesters of Substituted Glutaric Acids", Journal of Pharmaceutical Sciences, 69(5), 506-509 (1980).

Burk et al., "An Enantioselective Synthesis of (S)-(+)-3-Aminomethyl-5-methylhexanoic Acid via Asymmetric Hydrogenation", J. Org. Chem., 68(14): 5731-5734 (2003).

Cason, J. et al., "Branched-Chain Fatty Acids. XXVII. Further Study of the Dependence of Rate of Amide Hydrolysis on Substitution near the Amide Group. Relative Rates of Hydrolysis of Nitrile to Amide and Amide to Acid," J. Org. Chem., 18(9): 1129-1136 (1953).

Chen et al., "Synthesis of Pregabalin", Zhongguo Yiyao Gongye Zazhi, vol. 35, No. 4, pp. 195-196 (2004).

Colonge et al., "Preparation De Pyrrolidones-2 et de Gamma-Aminoacides," Bulletin De La Societe Chimique De France, Societe Francaise De Chimie, 598-603 (1962).

Day and Thorpe, "The Formation and Reactions of Imino-compounds. Part XX. The Condensation of Aldehydes with Cyanoacetamide," J. Chem. Soc., 117: 1465-1474 (1920).

Elinson et al., "Electrochemical Cyclization of Tetramethyl Esters of 2-Substituted Propane-1, 1, 3, 3-Tetracarboxylic Acids in the Presence of Salts of Hydrohalic Acids", Izvestiya Akademii Nauk SSSR, Seriya Khimicheskaya, 12, 2783-2789 (1990).

Hiratake et al., "Enantiotopic-group Differentiation. Catalytic Asymmetric Ring-opening of Prochiral Cyclic Acid Anhydrides with Methanol, using Cinchona Alkaloids", Journal of the Chemical Society, Perkin Trans. 1, 1053-1058 (1987).

Hoekstra, Marvin S. et al., "Chemical Development of Cl-1008, an Enantiomerically Pure Anticonvulsant", Organic Process Research & Development, Vol. 1, No. 1, pp. 26-38 (1997).

Karanewsky, D.S. et al., "Practical Synthesis of an Enantiomerically Pure Synthon for the Preparation of Mevinic Acid Analogues", J. Org. Chem., vol. 56, No. 11, pp. 3744-3747 (1991).

Knoevenagel, "Condensation zwischen Malonester und Aldehyden unter dem Einfluss von Ammoniak und organischen Aminen", Chemische Berichte, 31, 2585-2595 (1898).

Li et al., "Highly Enantioselective Catalytic Conjugate Addition of Malonate and β3-Ketoester to Nitroalkenes: Asymmetric C-C Bond Formation with New Bifunctional Organic Catalysts Based on Cinchona Alkaloids", J. Am. Chem. Soc., vol. 126, No. 32, pp. 9906-9907 (2004).

Lin et al., "Chiral HPLC Separations for Process Development of S-(+)-Isobutyl GABA, A Potential Anti-Epileptic Agent", J. Liq. Chrom. & Rel. Technol., 19(16), 2699-2708 (1996).

Liu, et al., 12 Tetrahedron: Asymmetry, pp. 419-426, 2001.

Martin, L. et al., "Pregabalin," Drugs of the Future, 24(8): 862-870 (1999).

Morissette, et al., Advanced Drug Delivery Reviews, vol. 56, pp. 275-300, 2004.

Okino et al., "Entantio- and Diastereoselective Michael Reaction of 1,3-Dicarbonyl Compounds to Nitroolefins Catalyzed by a Bifunctional Thiourea", J. Am.Chem.Soc., vol. 127, No. 1, pp. 119-125 (2005).

Ruhemann et al., "Formation of Ethereal Salts of Polycarboxylic Acids", *Journal of the Chemical Society*, 73, 1006-1016 (1898).

Sakurai, "Condensation of Ethyl Malonate and Ethyl Acetoacetate with Aliphatic Aldehydes by Potassium Fluoride", *Sci. Pap. I.P.C.R.*, 53, 250-255 (1959).

Sammis et al., "Highly Enantioselective Catalytic Conjugate Addition of Cyanide to α,β-Unsaturated Imides", J.Am.Chem.Soc., vol. 125, No. 15, pp. 4442-4443 (2003).

Serfass et al., "General Synthesis of 3-Substitued Alkenyl GABA as Potential Anticonvulsants," *Bioorganic & Medicinal Chemistry Letters* 8 (1998) 2599-2602.

Shintani et al., "Highly enantioselective desymmetrization of anhydrides by carbon nucleophiles: reactions of Grignard reagents in the presence of (−)-sparteine", Angewandte Chemie, International Edition, vol. 41, No. 6, pp. 1057-1059 (2002).

Snyder et al., Introduction to Modern Liquid Chromatography, 549-572 (2d ed., John Wiley & Sons, 1979).

Strobel et al., Chemical Instrumentation: A Systematic Approach, 391-393, 879-894, 922-925, 953 (3d ed. 1989).

Theisen, P.D. et al., "Prochiral Recognition in the Reaction of 3-Substituted Glutaric Anhydrides with Chiral Secondary Alcohols," *J. Org. Chem.*, 58(1): 142-146 (1993).

Verma et al., "Desymmetrization of Prochiral Anhydrides with Evans Oxazolidinones: an efficient route to homochiral glutaric and adipic acid derivatives", Journal of the Chemical Society, Perkin Transactions 1: Organic and Bio-Organic Chemistry, No. 3, pp. 257-264 (1999).

Vippagunta, et al., Advanced Drug Delivery Reviews, vol. 48, pp. 3-26, 2001.

Yamamoto et al., "Stereoselective Synthesis of (E)-Alkylidenesuccinates by Palladium-catalyzed Carbonylation", Bull.Chem.Soc.Japan., vol. 58, No. 11 pp. 3397-3398 (1985).

Yuen et al., "Enantioselective Synthesis of PD144723: A Potent Stereospecific Anticonvulsant", *Bioorganic & Medicinal Chemistry Letters*, 4(6), 823-826(1994).

\* cited by examiner

ASYMMETRIC SYNTHESIS OF (S)-(+)-3-(AMINOMETHYL)-5-METHYLHEXANOIC ACID

CROSS-REFERENCE TO RELATED APPLICATIONS

This application is a divisional of U.S. Ser. No. 12/290,286, filed Oct. 28, 2008, now U.S. Pat. No. 7,851,651 which is a divisional of U.S. Ser. No. 11/523,876, filed Sep. 19, 2006, now U.S. Pat. No. 7,446,220 which claims the benefit of priority to U.S. provisional application Ser. Nos. 60/718,689, filed Sep. 19, 2005; 60/754,392, filed Dec. 27, 2005; 60/763,593, filed Jan. 30, 2006; 60/752,434, filed Dec. 20, 2005; 60/753,220, filed Dec. 21, 2005; 60/763,696, filed Jan. 30, 2006; and 60/839,947, filed Aug. 23, 2006, herein incorporated by reference.

FIELD OF THE INVENTION

The invention encompasses processes for the synthesis of (S)-(+)-3-(aminomethyl)-5-methylhexanoic acid, (S)-Pregabalin, and intermediates of (S)-Pregabalin.

BACKGROUND OF THE INVENTION (S)-Pregabalin, (S)-(+)-3-(aminomethyl)-5-methylhexanoic acid, a compound having the chemical structure,

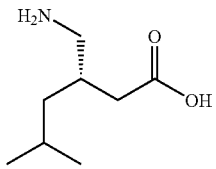

is also known as γ-amino butyric acid or (S)-3-isobutyl GABA. (S)-Pregabalin, marketed under the name LYRICA®, has been found to activate GAD (L-glutamic acid decarboxylase). (S)-Pregabalin has a dose dependent protective effect on-seizure, and is a CNS-active compound. (S)-Pregabalin is useful in anticonvulsant therapy, due to its activation of GAD, promoting the production of GABA, one of the brain's major inhibitory neurotransmitters, which is released at 30 percent of the brains synapses. (S)-Pregabalin has analgesic, anticonvulsant, and anxiolytic activity.

Several processes for the synthesis of (S)-Pregabalin are known. For example, see DRUGS OF THE FUTURE, 24 (8), 862-870 (1999). One such process is illustrated in scheme 1.

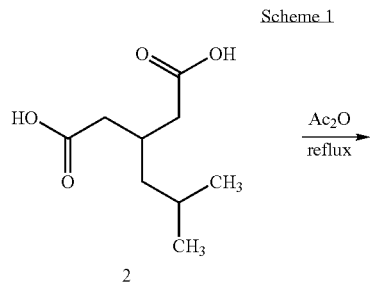

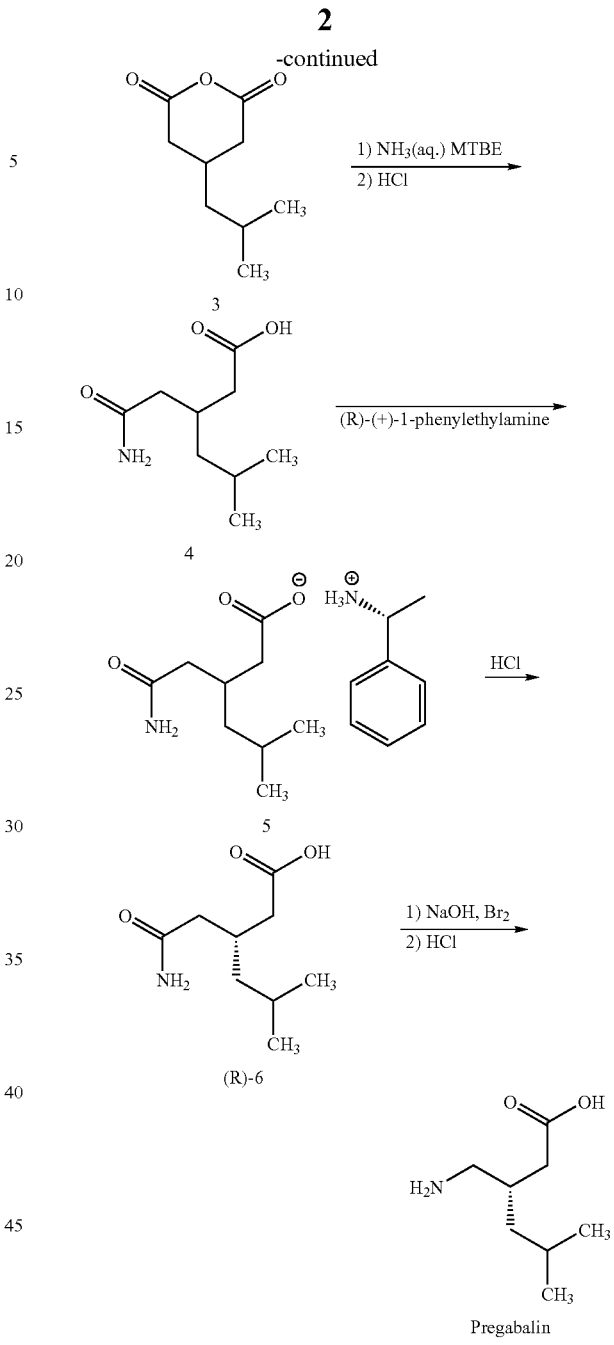

In Scheme 1, 3-isobutyl glutaric acid, compound 2, is converted into the corresponding anhydride, compound 3, by treatment with refluxing acetic anhydride. The reaction of the anhydride with $NH_4OH$ produces the glutaric acid monoamide, compound 4, which is resolved with (R)-1-phenylethylamine, yielding the (R)-phenylethylamine salt of (R)-3-(carbamoylmethyl)-5-methylhexanoic acid, compound 5. Combining the salt with an acid liberates the R enantiomer, compound 6. Finally, a Hoffmann degradation with $Br_2$/NaOH provides (S)-Pregabalin. A disadvantage of this method is that it requires separating the two enantiomers, thereby resulting in the loss of half the product, such that the process cost is high.

Several stereoselective processes for the synthesis of (S)-Pregabalin have been disclosed. For example, U.S. Pat. No. 5,599,973 discloses the preparation of (S)-Pregabalin using stoichiometric (+)-4-methyl-5-phenyl-2-oxazolidinone as a chiral auxiliary that may be recycled. In general, however, that route is of limited use for scale-up, principally due to the low temperature required for the reactions, the use of pyrophoric reagent, such as, butyl lithium, to side reactions, and due to a low overall yield.

Another process is disclosed in U.S. Patent Application Publication No. 2003/0212290, which discloses asymmetric hydrogenation of a cyano-substituted olefin, compound 7, to produce a cyano precursor of (S)-3-(aminomethyl)-5-methyl hexanoic acid, compound 8, as seen in scheme 2.

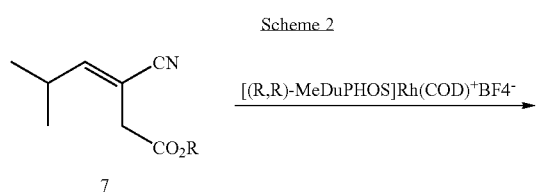

Subsequent reduction of the nitrile in compound 8 by catalytic hydrogenation produces (S)-Pregabalin. The cyano hexenoate starting material, compound 7, is prepared from 2-methyl propanal and acrylonitrile (Yamamoto et al, *Bull. Chem. Soc. Jap.*, 58, 3397 (1985)). However, the disclosed method requires carbon monoxide under high pressure, raising serious problems in adapting this scheme for production scale processes.

A process published by G. M. Sammis, et al., *J. Am. Chem. Soc.*, 125(15), 4442-43 (2003), takes advantage of the asymmetric catalysis of cyanide conjugate addition reactions. The method discloses the application of aluminum salen catalysts to the conjugate addition of hydrogen cyanide to α,β-unsaturated imides as shown in scheme 3. Reportedly, TMSCN is a useful source of cyanide that can be used in the place of HCN. Although the reaction is highly selective, this process is not practicable for large scale production due to the use of highly poisonous reagents. Moreover, the last reductive step requires high pressure hydrogen, which only adds to the difficulties required for adapting this scheme for a production scale process.

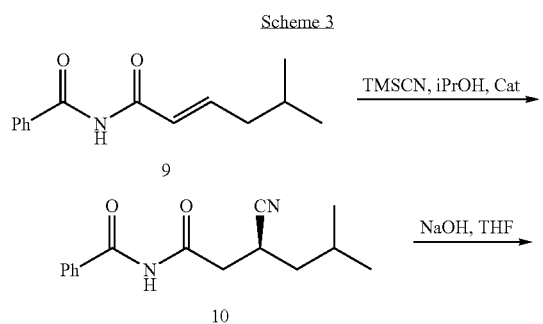

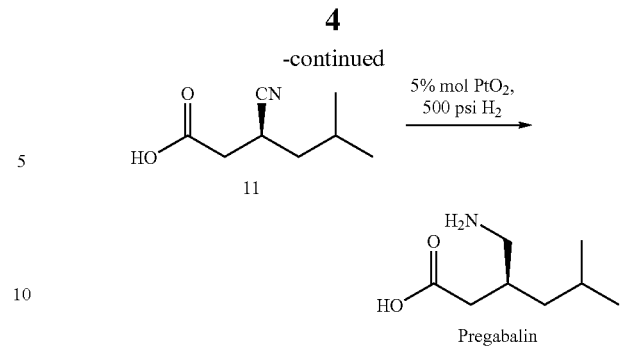

In 1989, Silverman reported a convenient synthesis of 3-alkyl-4-amino acids compounds in SYNTHESIS, Vol. 12, 953-944 (1989). Using 2-alkenoic esters as a substrate, a series of GABA analogs were produced by Michael addition of nitromethane to α,β-unsaturated compounds, followed by hydrogenation at atmospheric pressure of the nitro compound to amine moiety as depicted in scheme 4.

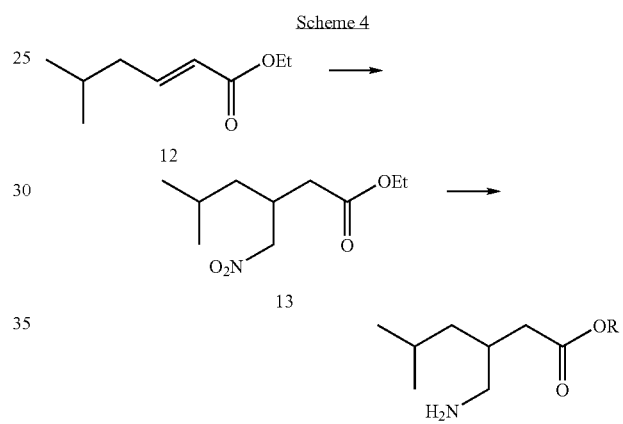

Further resolution of compound 14 may be employed to resolve Pregabalin. This, of course, results in the loss of 50 percent of the product, a serious disadvantage. However, the disclosed methodology reveals that the nitro compound can serve as an intermediate for the synthesis of 3-alkyl-4-amino acids.

Recent studies have indicated that cinchona alkaloids are broadly effective in chiral organic chemistry. A range of nitroalkenes were reportedly treated with dimethyl or diethyl malonate in THF in the presence of cinchona alkaloids to provide high enantiomeric selectivity of compound 15,

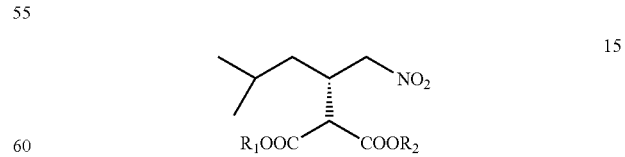

and its analogues. For example, see H. Li, et al., *J. Am. Chem. Soc.*, 126(32), 9906-07 (2004). These catalysts are easily accessible from either quinine or quinidine, and are reportedly highly efficient for a synthetically C—C bond forming asymmetric conjugate addition as shown in scheme 5.

Scheme 5

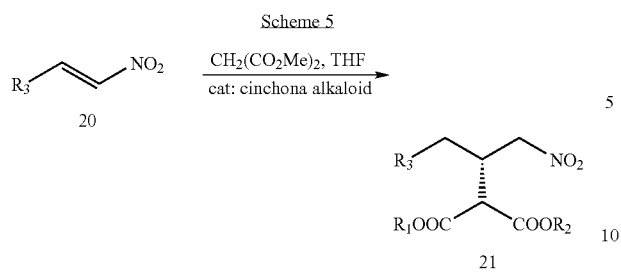

$R_3$ represents several alkyl and aryl groups. The scope of the reaction has been extended to other nitroolefins and applied to prepare ABT-546 employing bis(oxazoline)Mg $(OTf)_2$. See, for example, D. M. Barnes, et al., *J. Am. Chem. Soc.*, 124(44), 13097-13105 (2002).

Other groups have investigated a new class of bifunctional catalysts bearing a thiourea moiety and an amino group on a chiral scaffold. See T. Okino, et al., *J. Am. Chem. Soc.*, 127(1), 119-125 (2005). On the basis of a catalytic Michael addition to the nitroolefin with enantiomeric selectivity, they were able to prepare a series of analogues of compound 15.

Thus, there is a need in the art for new processes for the preparation of (S)-Pregabalin that does not suffer from the disadvantages mentioned above.

SUMMARY OF THE INVENTION

In one embodiment, the invention encompasses (3S)-5-methyl-3-(2-oxo-2{[(1S)-1-aryl-alkyl]amino}ethyl)hexanoic acid of the following formula 24,

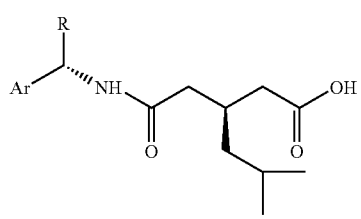

wherein Ar is a $C_{6-10}$ aromatic group, and R is a straight or branched $C_{1-4}$ alkyl, ester or carboxylic acid.

In another embodiment, the invention encompasses a (R)-3-isobutylpentanedioic acid amide-((S)-1-aryl-alkyl)amide of the following formula 25,

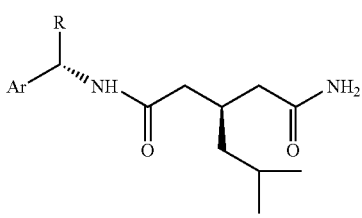

wherein Ar is a $C_{6-10}$ aromatic group, and R is a straight or branched $C_{1-4}$ alkyl, ester or carboxylic acid.

In another embodiment, the invention encompasses a (S)-4-methyl-2-{[((S)-1-aryl-alkyl-carbamoyl)-methyl]pentyl}carbamic acid methyl ester of the following formula 26,

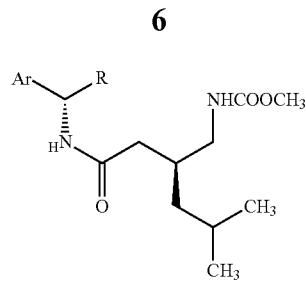

wherein Ar is a $C_{6-10}$ aromatic group, and R is a straight or branched $C_{1-4}$ alkyl, ester or carboxylic acid.

In another embodiment, the invention encompasses a (S)-2-carbamoylmethyl-4-methylpentyl)carbamic acid alkyl ester of the following formula 27,

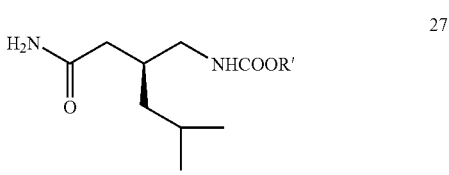

wherein R' is a straight or branched $C_{1-5}$ alkyl.

In another embodiment, the invention encompasses a process for preparing (S)-Pregabalin comprising: preparing a compound of the following formula 24

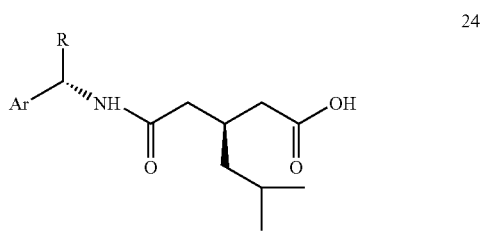

wherein Ar is a $C_{6-10}$ aromatic group and R is a straight or branched $C_{1-4}$ alkyl, ester, or carboxylic acid; converting the compound of formula 24 into a compound of the following formula 25, wherein Ar is a $C_{6-10}$ aromatic group, and R is a straight or branched $C_{1-4}$ alkyl, ester, or carboxylic acid;

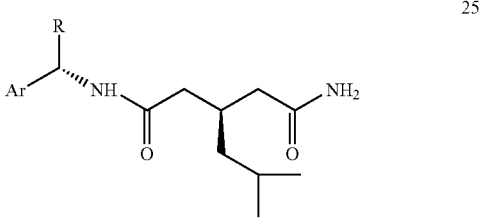

converting the compound of formula 25 into a compound of the following formula 26

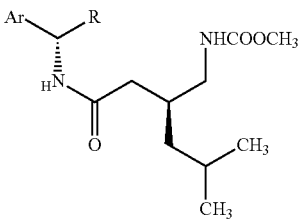

wherein Ar is a $C_{6-10}$ aromatic group, and R is a straight or branched $C_{1-4}$ alkyl, ester, or carboxylic acid; converting the compound of formula 26 into a compound of the following formula 27

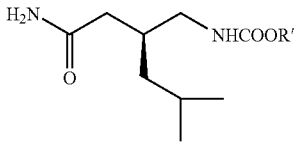

wherein R' is a straight or branched $C_{1-5}$ alkyl; and converting the compound of formula 27 into (S)-Pregabalin.

The compound of formula 24 is preferably prepared by a process comprising: combining a chiral amine of the following formula 23,

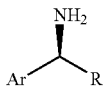

wherein Ar is a $C_{6-10}$ aromatic group, and R is a straight or branched $C_{1-4}$ alkyl, ester, or carboxylic acid, an organic solvent selected from at least one of $C_{6-10}$ aromatic hydrocarbons, substituted aromatic hydrocarbons, $C_{2-8}$ ethers, halogenated hydrocarbons, straight or branched $C_{1-4}$ alcohols, $C_{3-8}$ esters, straight, branched or cyclic $C_{1-6}$ alkanes, or $C_{3-8}$ ketones, and at least one base, to obtain a mixture; cooling the mixture to a temperature of about −70° C. to about 10° C.; adding 3-isobutyl glutaric anhydride to the mixture; maintaining the mixture at a temperature of about −70° C. to about 10° C. for at least about one hour to obtain the compound of formula 24; and recovering the compound of formula 24 from the mixture.

The compound of formula 24 is preferably converted into the compound of formula 25 by a process comprising: combining at a temperature of about 20° C. to about −30° C., the compound of formula 24 and at least one organic solvent selected from the group consisting of substituted aromatic hydrocarbons, $C_{6-10}$ aliphatic hydrocarbons, halogenated hydrocarbons, ethers and ketones, an amidation reagent selected from the group consisting of $C_{1-4}$ alkyl and $C_{6-8}$ aryl haloformates, and acid halides, and a base to form a mixture; maintaining the mixture for about one hour to about two hours at a temperature of about −10° C. to about 20° C.; adding ammonia to obtain the compound of formula 25; and recovering the compound of formula 25 from the mixture.

The compound of formula 25 is preferably converted into the compound of formula 26 by a process comprising: combining a solution of the compound of formula 25 in at least one straight or branched alkyl alcohol, such as methyl, ethyl, isopropyl, n-butyl, isobutyl, or t-butyl alcohol, preferably, methanol or ethanol, at a temperature of about −25° C. to about −45° C. with bromine, in the presence of at least one base, to obtain a basic mixture; warming the basic mixture to a temperature of about 50° C. to about 70° C., preferably, about 55° C. to about 60° C.; warming the basic mixture for about 1 hour to about 4 hours to obtain the compound of formula 26; and recovering the compound of formula 26 from the basic mixture. Preferably, the compound of formula 26 is obtained in a purity of about 90% to about 100% area by HPLC, more preferably, in a purity of about 92% to about 100% area by HPLC, and, most preferably, in a purity of about 95% to about 100% area by HPLC.

Preferably, the base is a metal alkoxide, such as sodium ethoxide, sodium methoxide, potassium methoxide, potassium ethoxide, or potassium tert-butoxide, and is preferably sodium ethoxide or sodium methoxide. Preferably, the compound of formula 26 is recovered by evaporating the solvent from the basic mixture to form a residue and extracting the compound of formula 26 from the residue. Preferably, the compound of formula 26 is extracted with dichloromethane, ethyl acetate, or toluene. The recovered compound of formula 26 is preferably crystallized from an organic solvent selected from at least one of ethers, esters, hydrocarbons, substituted hydrocarbons, and alcohols. Preferably, the organic solvent is diisopropyl ether, ethyl acetate, cyclohexane, dichloromethane, or methanol.

Preferably, the compound of formula 26 is converted into the compound of formula 27 by a process comprising: combining the compound of formula 26 and a mixture of water and an ether to obtain a mixture; combining the mixture with ammonia and an alkali metal at a temperature of about −30° C. to about −60° C., preferably, about −40° C. to about −30° C., to obtain a reaction mixture; maintaining the reaction mixture for about 4 to about 10 hours until the excess of ammonia is evaporated to obtain the compound of formula 27; and, preferably, recovering the compound of formula 27 from the reaction mixture. Preferably, the ether is tetrahydrofuran or dioxane. Preferably, the ammonia is liquid ammonia. *Preferably, the alkali metal is lithium or sodium. Preferably, the compound of formula* 27 *is recovered by extraction, and,* more preferably, the compound of formula 27 is crystallized from an ether, such as diisopropyl ether.

Preferably, the compound of formula 27 is converted to (S)-Pregabalin in a process comprising: combining the compound of formula 27 with an acid to obtain a mixture; maintaining the mixture at a temperature of about 60° C. to about 130° C., preferably, about 80° C. to about 110° C., for about 5 to about 30 hours, preferably, for about 18 to about 30 hours, and, more preferably, for about 5 to about 10 hours, to obtain (S)-Pregabalin; and recovering the (S)-Pregabalin from the mixture. Preferably, the acid is a strong mineral acid, such as hydrochloric acid or sulfuric acid.

Preferably, the (S)-Pregabalin is recovered by a process comprising: adjusting the pH of the mixture to about 3 to about 1; extracting a solution of (S)-Pregabalin from the mixture with an alcohol; adjusting the pH of the solution to about 4 to about 7 to induce the precipitation of (S)-Pregabalin; and recovering the precipitated (S)-Pregabalin. Preferably, the (S)-Pregabalin is obtained in a purity of at least about 98% area by HPLC, and, more preferably, about 99% to about 100% area by HPLC.

In another embodiment, the invention encompasses a process for preparing (S)-Pregabalin comprising: combining a compound of the following formula 26,

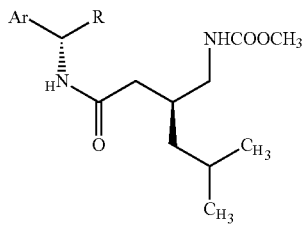

wherein Ar is a $C_{6-10}$ aromatic group, and R is a straight or branched $C_{1-4}$ alkyl, ester, or carboxylic acid, with an acid to obtain a mixture; maintaining the mixture at a temperature of about 60° C. to about 130° C., for about 3 hours to about 30 hours, to obtain (S)-Pregabalin; and recovering the (S)-Pregabalin from the mixture.

In another embodiment, the invention encompasses a process for recycling 3-isobutyl glutaric anhydride comprising: preparing a compound of formula 24 from 3-isobutyl glutaric anhydride by the process according to claim 29; crystallizing the recovered compound of formula 24 from an organic solvent; removing the crystals from the organic solvent; combining the remaining organic solvent with an acid to obtain a first mixture; maintaining the first mixture at a temperature of about 60° C. to about 130° C., to obtain 3-isobutyl glutaric acid; combining the 3-isobutyl glutaric acid with acetic anhydride to obtain a second mixture; heating the second mixture to a temperature of about 125° C. to about 145° C. to obtain 3-isobutyl glutaric anhydride; and recovering the 3-isobutyl glutaric anhydride from the second mixture.

In another embodiment, the invention encompasses (S)-pregabalin having an enantiomeric purity of about 99% to about 100% area by HPLC, preferably of about 99.9% to about 100% area by HPLC.

DETAILED DESCRIPTION OF THE INVENTION

Figure 1:
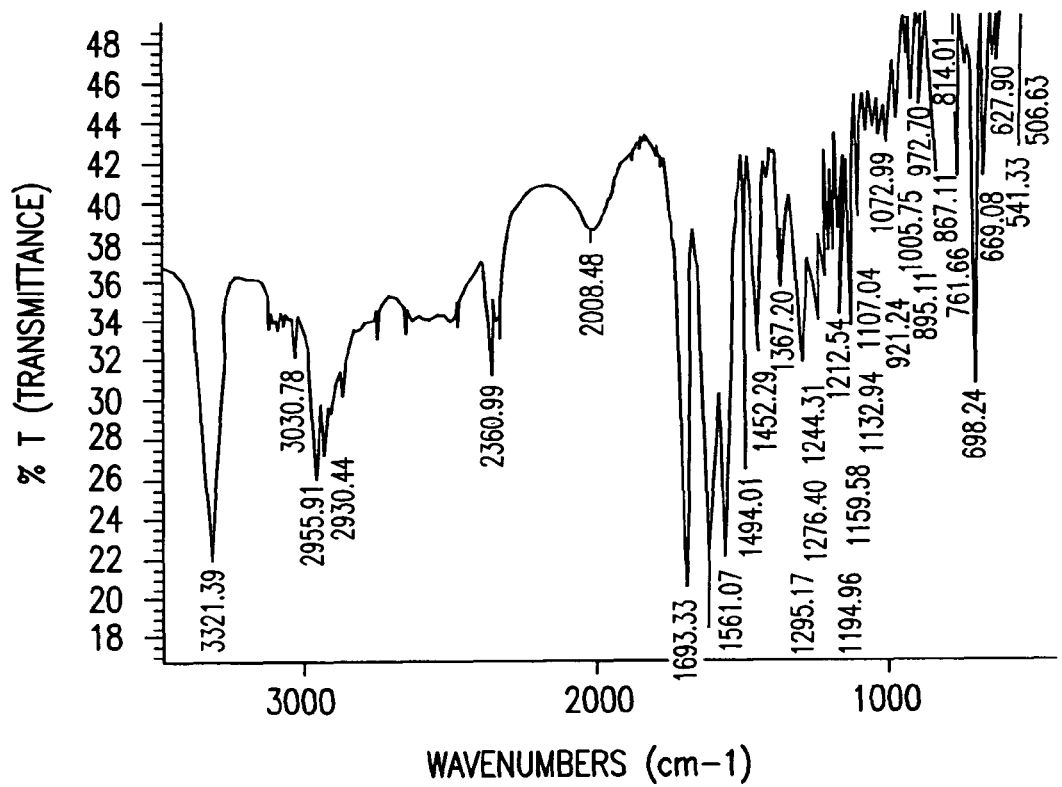
FIG. 1 illustrates an IR spectrum of (3S)-5-methyl-3-(2-oxo-2{[(1S)-1-phenylmethyl]amino}ethyl)hexanoic acid of formula 24A.
Figure 2:
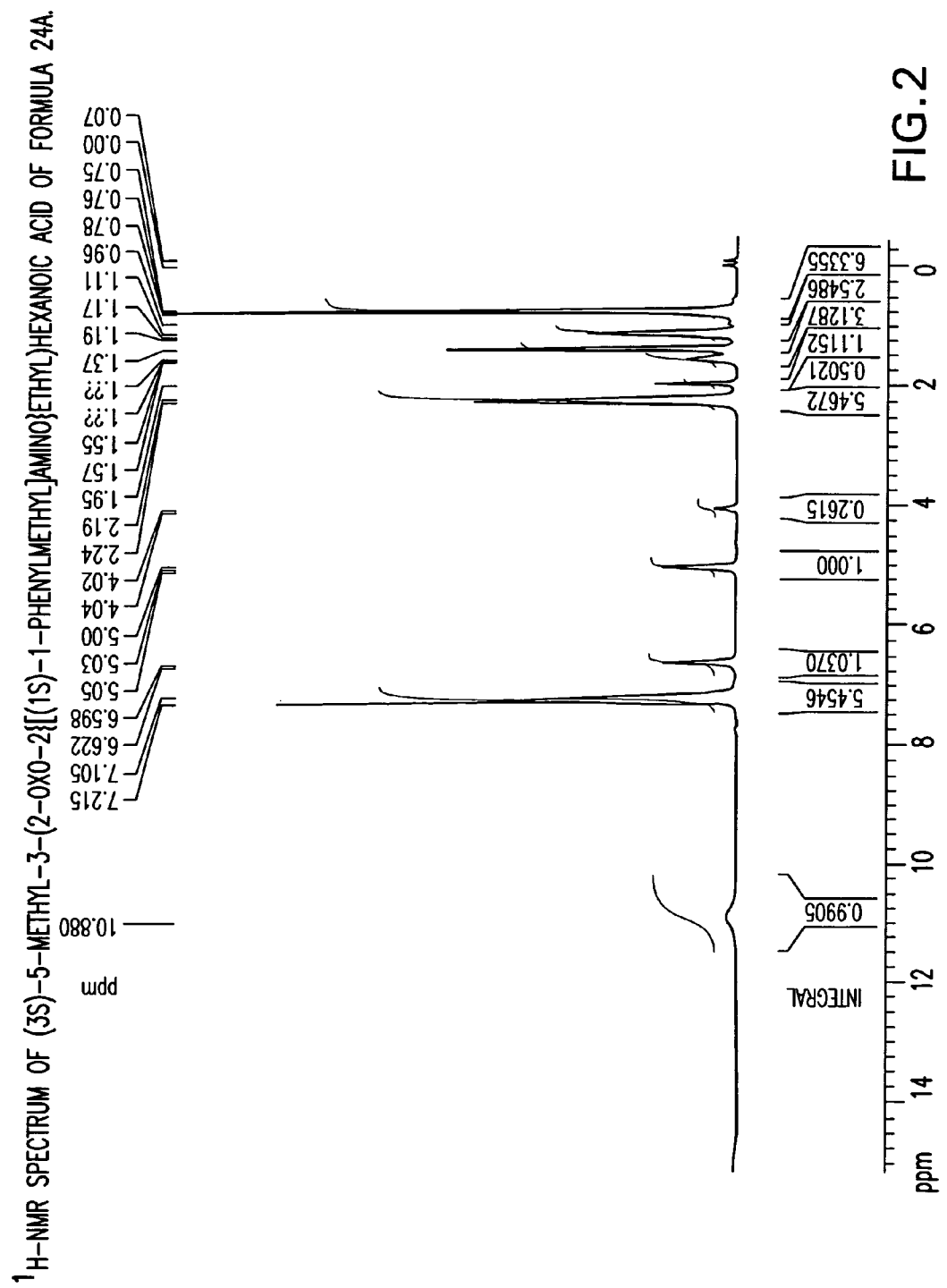
FIG. 2 illustrates a $^1$H-NMR spectrum of (3S)-5-methyl-3-(2-oxo-2{[(1S)-1-phenylmethyl]amino}ethyl)hexanoic acid of formula 24A.
Figure 3:
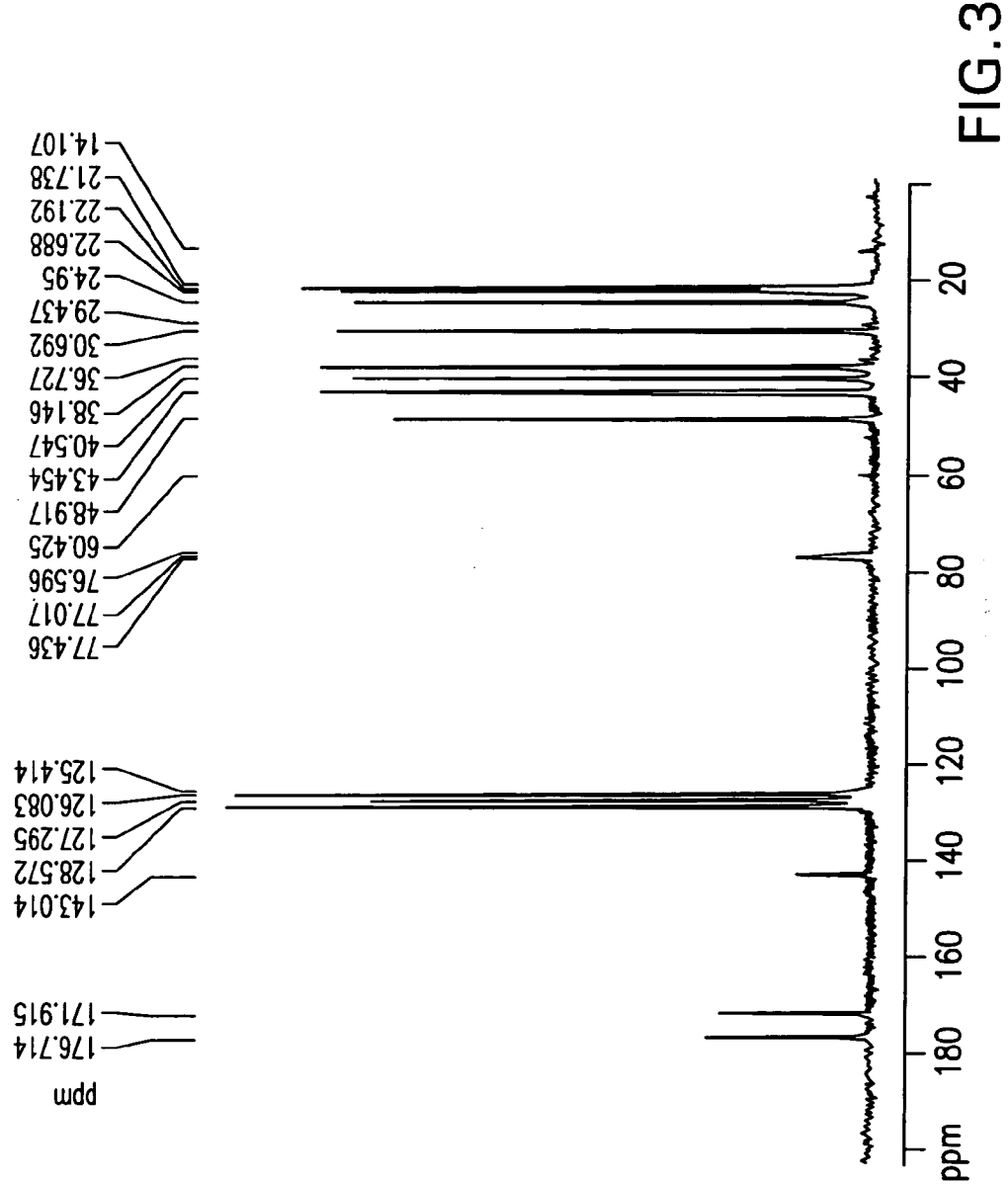
FIG. 3 illustrates a $^{13}$C-NMR spectrum of (3S)-5-methyl-3-(2-oxo-2{[(1S)-1-phenylmethyl]amino}ethyl)hexanoic acid of formula 24A.
Figure 4:
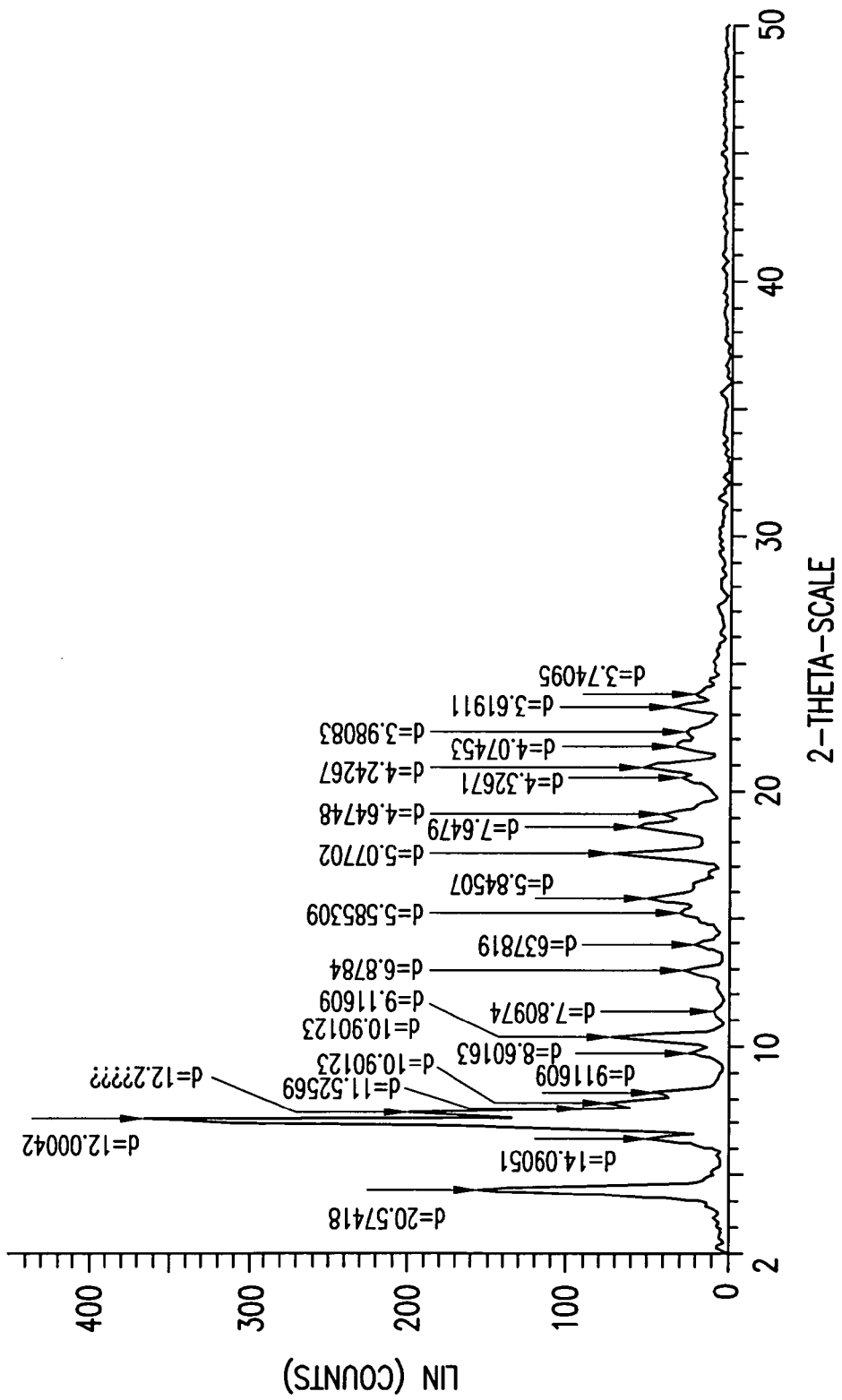
FIG. 4 illustrates a powder X-ray diffraction pattern of (3S)-5-methyl-3-(2-oxo-2{[(1S)-1-phenylmethyl]amino}ethyl)hexanoic acid of formula 24A.

The present invention provides a stereoselective synthesis of (S)-Pregabalin according to the following scheme:

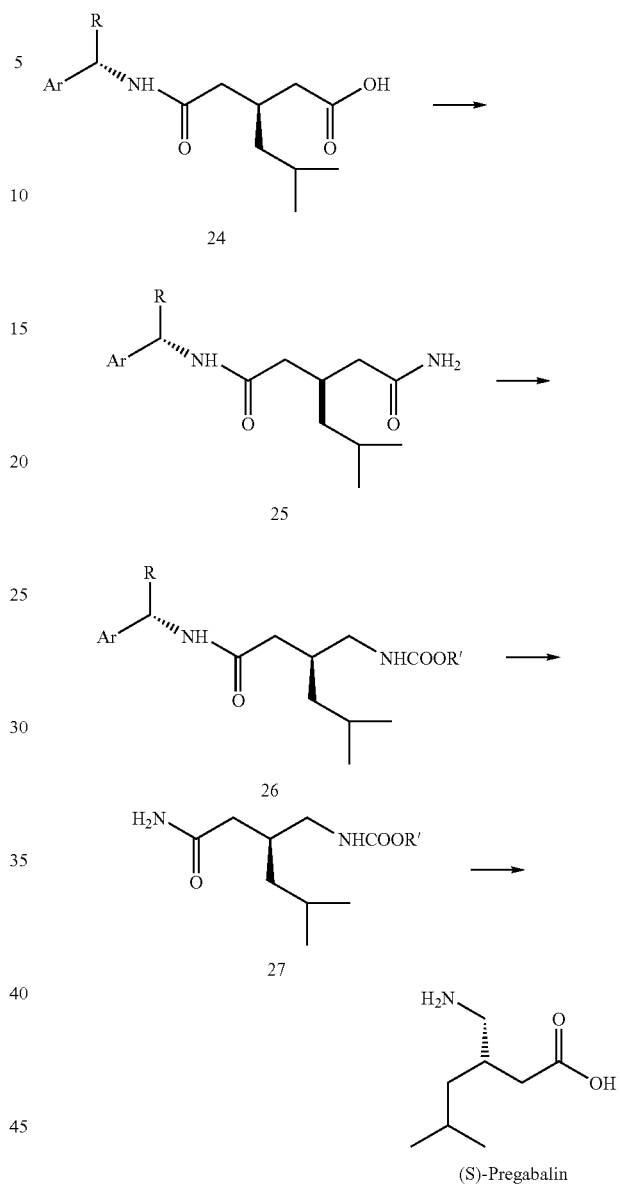

Scheme 6

This process allows for obtaining (S)-Pregabalin with a relatively high enantiomeric purity.

The invention encompasses (3S)-5-methyl-3-(2-oxo-2{[(1S)-1-aryl-alkyl]amino}ethyl)hexanoic acids of formula 24,

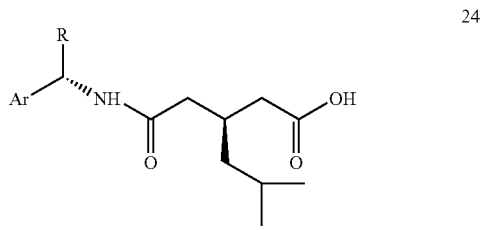

24 wherein Ar is a $C_{6-10}$ aromatic group and R is a straight or branched $C_{1-4}$ alkyl, ester, or carboxylic acid.

Preferably, the $C_{6-10}$ aromatic group is naphthyl, phenyl, substituted phenyl, or substituted naphthyl, more preferably phenyl. Preferably, the substituted phenyl is a phenyl group substituted with at least one of alkoxy, halogen, alkyl, carboxylic acid, or ester. A preferred alkoxy phenyl is methoxyphenyl. Preferred halogenated phenyls are chlorobenzene, bromobenzene, and fluorobenzene. Preferred alkylated phenyls are either toluene or ethylbenzene. Preferably, the carboxylic acid substituent is —COOH, —CH₂COOH, —CH(CH₃)COOH or —C(CH₃)₂COOH. Preferably the ester substituent is a methylester, ethylester, isopropylester, n-butylester, isobutyl, or t-butyl derivative of one of the above-listed carboxylic acid substituents.

Preferably, the $C_{1-4}$ alkyl is methyl, ethyl, isopropyl, n-butyl, isobutyl or t-butyl, more preferably, methyl.

When Ar is phenyl and R is methyl, the compound of formula 24 is (3S)-5-methyl-3-(2-oxo-2{[(1S)-1-phenylmethyl]amino}ethyl)hexanoic acid 24A

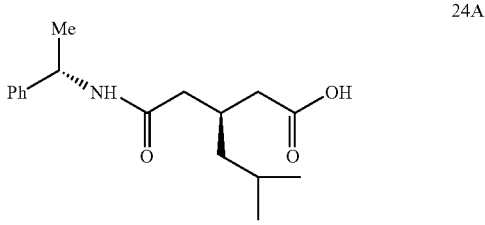

24A which may be characterized by data selected from: a $^{13}C$-NMR (CDCl₃, 300 MHz) spectrum having carbon chemical shifts at about 21.74, 22.19, 22.66, 24.95, 29.44, 30.89, 36.73, 38.15, 40.55, 43.45, 48.92, 125.41, 126.06, 127.29, 128.57, 143.01, 171.92 and 176.71 ppm; a $^1H$-NMR (CDCl₃, 75 MHz) spectrum having hydrogen chemical shifts at about 0.77, 1.18, 1.38, 1.56, 2.22, 5.03, 6.59-6.62, 7.11-7.22 and 10.88 ppm; and an IR spectrum having peaks at about 3321.39, 2955.91, 1693.33, 1617.43, 1561.07 and 698.24 $cm^{-1}$.

The invention also encompasses isolated (3S)-5-methyl-3-(2-oxo-2{[(1S)-1-phenylmethyl]amino}ethyl)hexanoic acid 24A, preferably in crystalline form. The crystalline form of 24A may be characterized by a powder X-ray diffraction pattern having peaks at about 4.3°, 6.9°, 7.2°, and 7.7° 2θ±0.2° 2θ. The crystalline form of 24A may be further characterized by X-ray powder diffraction peaks at about 6.3°, 8.1°, 9.7°, 10.3°, 11.3°, 12.9°, 13.9°, 15.1°, 15.7°, 17.5°, 18.6°, 19.1°, 20.5°, 20.9°, 21.8°, 22.3°, 23.3°, and 23.8° 2θ±0.2° 2θ. Moreover, the crystalline form of 24A may have a melting range of about 95° C. to about 98° C.

The invention also encompasses isolated (3S)-5-methyl-3-(2-oxo-2{[(1S)-1-phenylmethyl]amino}ethyl)hexanoic acid 24A having an optical purity of at least about 80% area by HPLC, preferably of at least about 93% area by HPLC, more preferably, of about 98% to about 100% area by HPLC, most preferably, of about 99% to about 100% area by HPLC.

The invention also encompasses (R)-3-isobutylpentanedioic acid amide-((S)-1-aryl-alkyl)amides of formula 25,

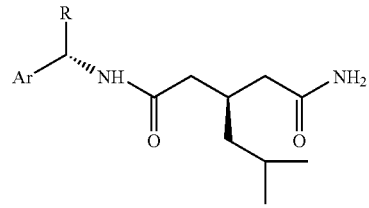

25 wherein Ar is a $C_{6-10}$ aromatic group, and R is a straight or branched $C_{1-4}$ alkyl, ester, or carboxylic acid.

Where Ar is phenyl and R is methyl, the compound of formula 25 is (R)-3-isobutylpentanedioic acid amide-((S)-1-phenylmethyl)amide 25A.

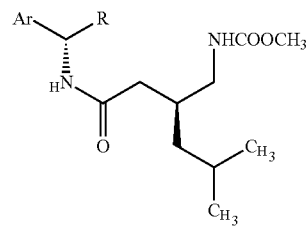

25A

The invention further encompasses (S)-4-methyl-2-{[((S)-1-aryl-alkyl-carbamoyl)-methyl]pentyl}carbamic acid methyl esters of formula 26,

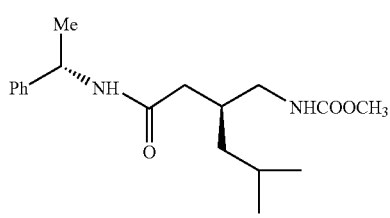

26 wherein Ar and R are as defined above for formula 24.

When Ar is phenyl and R and is methyl, the compound of formula 26 is (S)-4-methyl-2-[((S)-1-aryl-alkyl-carbamoyl)-methyl]pentyl}carbamic acid methyl ester 26A.

26A

The invention also encompasses (S)-2-carbamoylmethyl-4-methylpentyl)carbamic acid alkyl esters of formula 27,

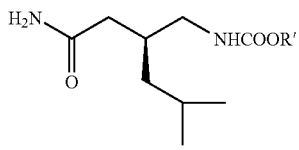

27 wherein R' is a straight or branched $C_{1-5}$ alkyl, preferably, methyl.

When R' is methyl, the compound of formula 27 is (S)-2-carbamoylmethyl-4-methylpentyl)carbamic acid methyl ester 27A.

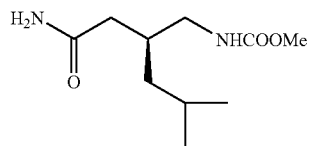

27A

Further, the invention encompasses a process for the preparation of (S)-Pregabalin via the intermediate compound of formula 24. The process comprises preparing the intermediate of formula 24, converting the intermediate compound of formula 24 into the diamide of formula 25, converting the diamide of formula 25 into the chiral carbamate of formula 26, converting the chiral carbamate into the compound of formula 27, and converting the compound of formula 27 into (S)-Pregabalin. Although each of the compounds of formula 24, formula 25, formula 26, and formula 27 can be isolated prior to conversion, isolation of the compounds of formula 26 and formula 27 is not required. Therefore, once the compound of formula 25 has been prepared and isolated, the preparation of the compound of formula 27 from the compound of formula 25 or the compound of formula 26 and the preparation of (S)-Pregabalin from the compound of formula 25 or the compound of formula 26 does not require isolation of any of the intermediate compounds. Thus, once the compound of formula 25 has been prepared and isolated, (S)-Pregabalin can be prepared in a one-pot process without the isolation of either of the compounds of formula 26 or formula 27.

The intermediate compound of formula 24 may be prepared by combining a chiral amine of formula 23,

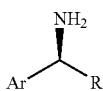

23 an organic solvent selected from at least one of $C_{6-10}$ aromatic hydrocarbons, substituted aromatic hydrocarbons, $C_{2-8}$ ethers, halogenated hydrocarbons, straight or branched $C_{1-4}$ alcohols, $C_{3-8}$ esters, straight, branched or cyclic $C_{1-6}$ alkanes, or $C_{3-8}$ ketones, and at least one base, to obtain a mixture, cooling the mixture, and adding 3-isobutyl glutaric anhydride of formula 22

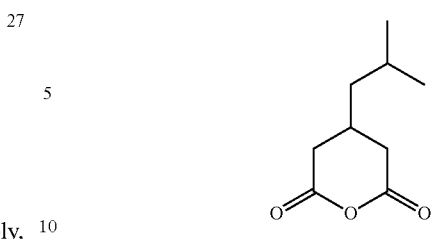

22 to the mixture to obtain the compound of formula 24,

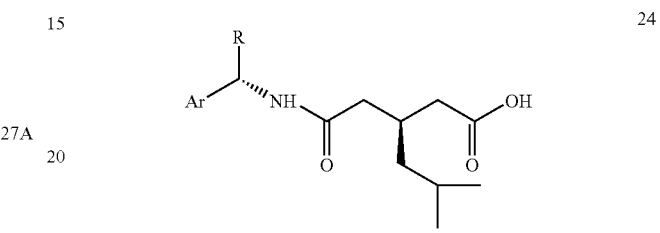

24 which is then recovered.

The 3-isobutyl glutaric anhydride of formula 22 may be prepared according to the process disclosed in U.S. Pat. No. 5,616,793.

The chiral amine of formula 23 is commercially available, and is used as a chiral auxiliary is a primary amine or a chiral amino acid derivative, wherein Ar and R are as defined above for the compound of formula 24. Preferably, the chiral amine of formula 23 is methylbenzylamine, and more preferably the chiral amine of formula 23 is (S)-methylbenzylamine.

Preferably, the aromatic group is toluene. The preferred ether is selected from tert-butyl methyl ether, tetrahydrofuran, diisopropyl ether, and diethyl ether. Preferably, the halogenated hydrocarbon is dichloromethane. Preferred $C_{1-4}$ alcohols are isopropyl alcohol, ethanol, methanol, or n-butanol. Preferably, the ester is selected from ethyl acetate, isopropyl acetate, and isobutyl acetate. A preferred straight, branched or cyclic $C_{1-6}$ alkane is either hexane or cyclohexane. Preferred ketones are selected from acetone, methyl isobutyl ketone, and methyl ethyl ketone. The more preferred organic solvent is toluene.

Preferably, the base is an organic base selected from diethyl amine, triethyl amine, di-n-propyl amine, di-isopropyl amine, tertbutylamine, morpholine, piperidine, pyridine, and 4-dimethyl aminopyridine. The most preferred base is 4-dimethyl aminopyridine.

Preferably, the mixture is cooled to a temperature of about –70° C. to about 10° C. before adding the 3-isobutyl glutaric anhydride.

Preferably, the mixture is maintained at a temperature of about –70° C. to about 10° C., more preferably of about 0° C. to about –50° C. and most preferably of about –40° C. to –30° C., before recovering the compound of formula 24. Preferably, the mixture is maintained for at least about one hour, more preferably about one hour to about six hours, most preferably, about one hour to about two hours, before recovering the compound of formula 24.

The order of combining the reacting substances when preparing the compound of formula 24 may influence the purity and the yield of the final product. Preferably, the chiral amine of formula 23 is combined with the base, followed by the addition of the 3-isobutylglutaric anhydride of formula 22.

The compound of formula 24 may be recovered by any method known in the art, such as extracting the organic phase with an aqueous basic solution to convert the acidic product to a salt, and acidifying the aqueous phase with a mineral acid to obtain back the acid product.

The compound of formula 24 may optionally be further purified by a crystallization from an organic solvent selected from at least one of esters, nitriles, ethers, $C_{4-6}$ straight, branched, or cyclic hydrocarbons, and $C_{6-10}$ substituted aromatic hydrocarbons. A preferred ester is ethyl acetate. Preferably, the nitrile is acetonitrile. A preferred ether is methyl t-butyl ether. A preferred $C_{6-8}$ substituted aromatic group is either toluene or xylene. Preferred mixtures are that of xylene and ethyl acetate, hexane and ethyl acetate, cyclohexane and ethyl acetate, and toluene and ethyl acetate. The most preferred mixture is that of toluene and ethyl acetate.

The compound of formula 24 obtained by the above-described process has an optical purity of at least about 80% area by HPLC, preferably of at least about 93% area by HPLC, more preferably of about 98% to about 100% area by HPLC, and most preferably of about 99% to about 100% area by HPLC.

The recovered compound of formula 24 is then converted to the diamide of formula 25,

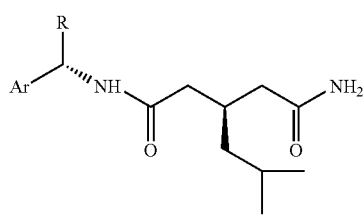

in a process comprising combining a mixture of the compound of formula 24 and at least one organic solvent selected from substituted aromatic hydrocarbons, $C_{6-10}$ aliphatic hydrocarbons, halogenated hydrocarbons, ethers and ketones, an amidation reagent selected from $C_{1-4}$ alkyl and $C_{6-8}$ aryl haloformates, and acid halides, and at least one base, and adding ammonia to obtain the compound of formula 25, which is then recovered.

Preferably, the ammonia is provided in an aqueous solution, i.e., ammonium hydroxide.

Preferably, the $C_{1-4}$ alkyl halo formate is a ethyl or methyl derivative of a chloro or bromoformate. Preferably, the $C_{6-8}$ aryl halo formate is a benzyl chloro or bromoformate. Preferred acid halides are acetyl, pivaloyl, oxaloyl or benzoyl chlorides and bromides. The most preferred haloformate is either ethylchloroformate or methylchloroformate. The more preferred acid halide is acetyl, pivaloyl, oxaloyl, or benzoyl chlorides. The most preferred amidation reagent is either ethylchloroformate or methylchloroformate.

Preferably, the substituted aromatic hydrocarbon is either toluene or xylene. A preferred $C_{6-10}$ aliphatic hydrocarbon is either hexane or heptane. Preferred ketones are acetone, methyl ethyl ketone, or methyl isobutyl ketone. Preferably, the ether is diethyl ether, diisopropyl ether, or tert-butyl methyl ether. Preferably, the halogenated hydrocarbon is dichloromethane. The more preferred organic solvent is either acetone or dichloromethane.

Preferably, the base is an organic base selected from diethyl amine, triethyl amine, di-n-propyl amine, di-isopropyl amine, tri-n-butyl amine, morpholine, piperidine, pyridine, and 4-dimethyl aminopyridine. The preferred base is either 4-dimethyl aminopyridine or triethyl amine.

Preferably, the mixture of the compound of formula 24 and an organic solvent is combined with the amidation reagent and the base at a temperature of about 20° C. to about −30° C., more preferably, of about −10° C. to about −20° C. Preferably, the compound of formula 24 is compound 24A.

Preferably, the mixture is maintained at a temperature of about −10° C. to about −20° C. before the addition of ammonia. Preferably, the mixture is maintained for about one hour to about two hours before the addition of ammonia.

The compound of formula 25 may be recovered by known methods in the art, such as, filtering and drying.

The compound of formula 25 is obtained by the above process having a purity of at least about 80% area by HPLC, more preferably of at least about 95% area by HPLC.

Then, the recovered compound of formula 25 is reacted with bromine in a Hoffman reaction under basic conditions. The process comprises combining a solution of a compound of formula 25 in at least one straight or branched alkyl alcohol with bromine, in a presence of at least one base, to obtain a basic mixture, and warming the basic mixture to obtain the chiral carbamate of formula 26,

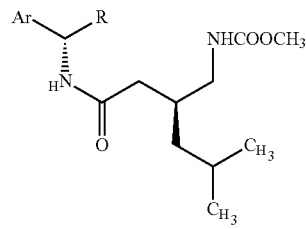

which is then recovered.

Preferably the combining step is performed at a temperature of about −25° C. to about −45° C.

Preferably, the base is a metal alkoxide selected from sodium ethoxide, sodium methoxide, potassium methoxide, potassium ethoxide, and potassium tert-butoxide. The more preferred base is either sodium ethoxide or sodium methoxide.

Preferably, the basic mixture is warmed to a temperature of about 50° C. to about 70° C., more preferably to a temperature of about 55° C. to about 60° C.

Preferably, the straight or branched alkyl alcohol is methyl, ethyl, isopropyl, n-butyl, isobutyl, or t-butyl alcohol, more preferably methanol or ethanol.

Preferably, the basic mixture is warmed for about 1 hour to about 4 hours before recovering the compound of formula 26.

The compound of formula 26 may be recovered by evaporating the solvent and further extracting with a solvent selected from dichloromethane, ethylacetate and toluene, followed by drying over a drying agent, such as, magnesium sulfate, followed by evaporating the solvent.

The recovered compound of formula 26 may be purified by crystallization from at least one of an ether, ester, hydrocarbone, substituted hydrocarbon, or alcohol. Preferably, the compound of formula 26 is crystallized from at least one of diisopropyl ether, ethyl acetate, cyclohexane, dichloromethane, or methanol.

The compound of formula 26 is obtained by the above process having a purity of at least about 80% area by HPLC, preferably of about 90% to about 100%, area by HPLC, more preferably of about 92% to about 100% area by HPLC, and most preferably, of about 95% to about 100% area by HPLC.

The amide moiety of the recovered compound of formula 26 is then converted to a primary amide moiety, to give the compound of formula 27

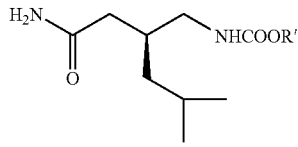

in a process comprising combining the compound of formula 26 and a mixture of water and an ether to obtain a mixture, combining the mixture with ammonia and an alkali metal to obtain a reaction mixture, and evaporating the excess of ammonia to obtain the compound of formula 27.

Preferably, the mixture containing the compound of formula 26 and a mixture of water and ether is combined with ammonia and an alkali metal at a temperature of about −30° C. to about −60° C., more preferably at a temperature of about −40° C. to about −30° C.

Preferably the ether is either tetrahydrofuran or dioxane.

Preferably the ammonia is liquid.

The preferred alkali metal is either lithium or sodium.

Preferably, the excess ammonia is evaporated by maintaining the reaction mixture for about 4 to about 10 hours.

The compound of formula 27 may be recovered by any known method in the art, such as, extraction and drying over anhydrous sodium sulfate.

The compound of formula 27 may optionally be purified by crystallization from ether, preferably, diisopropyl ether.

The compound of formula 27 is then converted to (S)-Pregabalin in a process comprising combining the compound of formula 27 with an acid to obtain a mixture and recovering (S)-Pregablin from the mixture.

Preferably, the acid is a strong mineral acid, more preferably either hydrochloric acid or sulfuric acid.

Preferably, the mixture is maintained at a temperature of about 60° C. to about 130° C., more preferably of about 80° C. to about 110° C., before recovering the (S)-Pregabalin.

Preferably, the mixture is maintained for about 5 to about 30 hours before recovering the (S)-Pregabalin.

Preferably, the mixture is maintained for about 18 to about 30 hours, when the mineral acid is hydrochloric acid and for about 5 to about 10 hours, when the mineral acid is sulfuric acid, before recovering the (S)-Pregabalin.

(S)-Pregabalin may be recovered by adjusting the pH of the mixture to about 3 to about 1, preferably by addition of a strong base; extracting a solution of (S)-Pregabalin from the mixture with an alcohol; adjusting the pH of the solution to about 4 to about 7, preferably with an inorganic or an organic base, to induce the precipitation of (S)-Pregabalin; and recovering the precipitated (S)-Pregabalin.

(S)-Pregabalin obtained by the above process has at least about 80% enantiomeric purity by area HPLC, preferably at least about 93% area by HPLC, more preferably, about 98% to about 100% area by HPLC, even more preferably, about 99% to about 100% area by HPLC, and most preferably of about 99.9% to about 100% area by HPLC.

In an alternative process, the chiral carbamate compound of formula 26 may be converted directly to (S)-Pregabalin. The process comprises combining the compound of formula 26 with an acid to obtain a mixture and maintaining the obtained mixture at a temperature of about 60° C. to about 130° C., for about 3 hours to about 30 hours, to obtain (S)-Pregabalin, which is then recovered.

Preferably, the acid is a strong mineral acid. Preferably, the strong mineral acid is selected from a group consisting of hydrochloric acid, hydrobromic acid, and sulfuric acid.

Preferably, the mixture is maintained at temperature of about 80° C. to about 125° C.

Preferably, the mixture is maintained for about 10 to about 30 hours when the mineral acid is hydrochloric acid, for about 5 to about 10 hours when the mineral acid is sulfuric acid, and for about 3 hours when the mineral acid is hydrobromic acid.

(S)-Pregabalin may be recovered by the same method described for the reaction of converting the compound of formula 27 to (S)-Pregabalin.

Further, 3-isobutyl glutaric anhydride of formula 22 can be regenerated by a process comprising the steps of combining the filtrate obtained from the crystallization process of compound of formula 24A with an acid to form a first mixture, recovering 3-isobutyl glutaric acid of the following formula 28

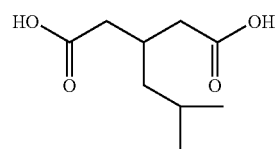

from the first mixture, combining the 3-isobutyl glutaric acid with acetic anhydride to obtain a second mixture, and recovering 3-isobutyl glutaric anhydride of formula 22 from the second mixture, which may then be reused.

Preferably, the acid is a strong mineral acid, more preferably either a 4 N to 12 N hydrochloric acid or 20 percent to 80 percent sulfuric acid.

Preferably the first mixture is maintained at a temperature of about 60° C. to about 130° C. before recovering the 3-isobutyl glutaric acid. Preferably, when the mineral acid is hydrochloric acid, the first mixture is maintained at temperature of about 100° C. to about 110° C. before recovering the 3-isobutyl glutaric acid. Preferably, when the mineral acid is sulfuric acid, the first mixture is maintained at a temperature of about 60° C. to about 130° C. before recovering the 3-isobutyl glutaric acid.

Preferably, the second mixture is heated to a temperature of about 125° C. to about 145° C., more preferably, of about 130° C. to about 140° C., before recovering the 3-isobutyl glutaric anhydride.

The 3-isobutyl glutaric anhydride may be recovered by any method known in the art, such as, distilling the excess of acetic anhydride and cooling.

In yet another embodiment, the present invention provides pharmaceutical compositions comprising enantiomerically pure (S)-Pregabalin and at least one pharmaceutically acceptable excipient. Such (S)-Pregabalin has at least about 80% enantiomeric purity, preferably of at least about 93% area by HPLC, more preferably, of about 98% to about 100% area by HPLC, even more preferably, of about 99% to about 100% area by HPLC, and most preferably of about 99.9% to about 100% area by HPLC. Such pharmaceutical composition can be prepared by combining (S)-Pregabalin with one or more excipients or adjuvants. Selection of excipients and the amounts to use may be readily determined by the formulation scientist based upon experience and consideration of standard procedures and reference works in the field.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease the release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be died using any pharmaceutically acceptable colorant to improve their appearance and/or facilitate patient identification of the product and unit dosage level.

In liquid pharmaceutical compositions of the present invention, the active ingredient and any other solid excipients are suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxy toluene, butylated hydroxyanisole, and ethylenediamine tetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate, or sodium acetate.

Selection of excipients and the amounts used may be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages may be conveniently presented in unit dosage form and prepared by any of the methods well known in the pharmaceutical arts.

Dosage forms include solid dosage forms like tablets, powders, capsules, suppositories, sachets, troches, and losenges, as well as liquid syrups, suspensions, and elixirs.

The dosage form of the present invention may be a capsule containing the composition, preferably a powdered or granulated solid composition of the invention, within either a hard or soft shell. The shell may be made from gelatin, and, optionally, contain a plasticizer such as glycerin and sorbitol, and an opacifying agent or colorant.

The active ingredient and excipients may be formulated into compositions and dosage forms according to methods known in the art.

A composition for tableting or capsule filling can be prepared by wet granulation. In wet granulation, some or all of the active ingredients and excipients in powder form are blended, and then further mixed in the presence of a liquid, typically water, that causes the powders to clump into granules. The granulate is screened and/or milled, dried, and then screened and/or milled to the desired particle size. The granulate may then be tabletted or other excipients may be added prior to tabletting, such as a glidant and/or a lubricant.

A tabletting composition can be prepared conventionally by dry blending. For example, the blended composition of the actives and excipients may be compacted into a slug or a sheet, and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tabletting include microcrystalline cellulose, spray dried lactose, dicalcium phosphate dihydrate and colloidal silica. The proper use of these and other excipients in direct compression tabletting is known to those in the art with experience and skill in particular formulation challenges of direct compression tabletting.

A capsule filling of the present invention may comprise any of the aforementioned blends and granulates that were described with reference to tabletting, however, they are not subjected to a final tabletting step.

In another embodiment, the present invention provides a method of treating a patient comprising administering to a patient in need thereof a therapeutically effective amount of the above crystalline form of O-desmethylvenlafaxine. Preferably, the patient suffers from a condition which may be treated with a norepinephrine or a serotonin re-uptake inhibitor. Such patient may be suffering from depression.

The following non-limiting examples are merely illustrative of the preferred embodiments of the present invention, and are not to be construed as limiting the invention, the scope of which is defined by the appended claims.

| Chiral HPLC analysis | |
|---|---|
| Instrument: | Waters-2487 |
| Column: | CHIRAL PACK AD-H, 250 × 4.6 mm, 5 μm |
| Mobile phase: | 2% TFA in n-Hexane/Ethanol - 95/5 |
| Flow: | 0.5 ml/minute |
| Temperature: | 30° C. |
| Wavelength: | 210 nm/UV visible spectrophotometer |

| F2-Acquisition parameters | | F2-Processing parameters | |
|---|---|---|---|
| $^1$H-NMR analysis | | | |
| Instrument | dpx 300 | SI | 32768 |
| Probhd | 5 mm Dual Z5 | SF | 300.13000292 MHz |
| Pulprog | zg | WDW | EM |
| TD | 16384 | SSB | 0 |
| Solvent | CDCl$_3$ | LB | 0.50 Hz |
| NS | 8 | GB | 0 |
| DS | 0 | PC | 1.4 |
| SWH | 8992.806 Hz | | |
| FIDRES | 0.548877 Hz | | |
| AQ | 0.9110004 sec | | |
| RG | 32 | | |
| DW | 55.600 μsec | | |
| DE | 4.50 μsec | | |
| TE | 300.0K | | |
| D1 | 5 sec | | |
| P1 | 11.35 μsec | | |
| SFO1 | 300.1342018 MHz | | |
| NUC1 | 1 H | | |
| PL1 | 0 dB | | |
| $^{13}$C-NMR analysis | | | |
| Instrument | dpx 300 | SI | 16384 |
| Probhd | 5 mm Dual Z5 | SF | 75.4677549 MHz |
| Pulprog | zgdc | WDW | EM |
| TD | 16384 | SSB | 0 |
| Solvent | CDCl$_3$ | LB | 10.00 Hz |
| NS | 5043 | GB | 0 |
| DS | 0 | PC | 1.4 |
| SWH | 18832.393 Hz | | |
| FIDRES | 1.149438 Hz | | |
| AQ | 0.4350452 sec | | |
| RG | 5792.6 | | |
| DW | 26.550 μsec | | |
| DE | 4.50 μsec | | |
| TE | 300.0K | | |
| D11 | 0.03 sec | | |
| PL12 | 17.8 Db | | |
| Cpdprg2 | waltz 16 | | |
| PCPD2 | 90.00 μsec | | |
| SFO2 | 300.1330013 MHz | | |
| NUC2 | 1 H | | |
| PL2 | 0 dB | | |
| D1 | 1 sec | | |
| P1 | 9.4 μsec | | |
| DE | 4.5 μsec | | |
| SFO1 | 75.4767751 MHz | | |
| NUC1 | 13 C | | |
| PL1 | 0 dB | | |

| IR analysis | |
|---|---|
| KBr pellets | |
| Number of sample scans | 16 |
| Number of background scans | 16 |
| Scanning parameters | 4000-500 cm$^{-1}$ |
| Resolution | 4 |
| Sample gain | 8 |
| Mirror velocity | 0.6329 |
| Aperture | 100 |
| X-ray analysis | |
| Instrument | SIEMENS "Model: D-5000 |
| Copper radiation | 1.5406 A |
| Scanning parameters | 2-50° 2θ. |
| Step scan | 0.03° |
| Step time | 0.5 second |

EXAMPLES

Example 1

Preparation of (3S)-5-methyl-3-(2-oxo-2{[(1S)-1-phenylethyl]amino}ethyl) hexanoic acid compound (24)

A three-necked flask equipped with an addition funnel, thermometer pocket, drying tube and a mechanical stirrer, was charged with toluene (400 ml), (S)-(−)-phenylethylamine (142.35 g, 1.1764 mole), and 4-dimethylaminopyridine (0.7176 g, 0.0059 mole). The mixture was cooled to a temperature of −10° C. to −15° C., followed by addition of a solution of 3-isobutyl glutaric anhydride (100 g, 0.59 mole) in toluene (100 ml), over a period of 45-60 minutes, and stirring for additional 1.5-2 hours, at a temperature of −10° C. to −15° C. The mixture was then extracted with 10% aqueous solution of NaOH (500 ml), and the aqueous phase was washed with toluene (1×250 ml). The pH of the aqueous phase was adjusted to 2-2.5 by adding a solution of hydrochloric acid (1-12 N). The aqueous phase was further extracted with toluene (1×800 ml) at a temperature of 70-80° C. The toluene layer was washed with 10% sodium chloride solution {700 ml) at a temperature of 70-80° C. followed by crystallization to get 125 g (73.0% yield) of a white solid of (3S)-5-methyl- 3-(2-oxo-2-{[(1S)-1-phenylethyl]amino}ethyl) hexanoic acid with an optical purity of 99.75%, as measured by chiral HPLC.

Example 2

Preparation of (3S)-5-methyl-3-(2-oxo-2{[(1S)-1-phenylethyl]amino}ethyl) hexanoic acid compound (24)

A three-necked flask equipped with an addition funnel, thermometer pocket, drying tube and a mechanical stirrer, was charged with toluene (400 ml), (S)-(–)-phenylethylamine (38.59 g, 0.0319 mole), and 4-dimethylaminopyridine (0.358 g, 0.0029 mole). The mixture was cooled to a temperature of –40° C. to –50° C., followed by addition of a solution of 3-isobutyl glutaric anhydride (50 g, 0.294 mole) in toluene (100 ml), over a period of 45-60 minutes, and stirring for additional 1.5-2 hours, at a temperature of –40° C. to –50° C. The mixture was then extracted with 3.5-4.0% aqueous solution of NaOH (1000 ml), and the aqueous phase was washed with toluene (1×250 ml). The pH of the aqueous phase was adjusted to 2-2.5 by adding a solution of hydrochloric acid (1-12 N). The aqueous phase was further extracted with ethyl acetate (1×300 ml and 1×100 ml), followed by drying the combined ethyl acetates extracts over anhydrous sodium sulphate, and stripping off the solvents to obtain a residue. The residue was crystallized from ethyl acetate and toluene mixture to get 60.7 g (71.0% yield) of a white solid of (3S)-5-methyl-3-(2-oxo-2-{[(1S)-1-phenylethyl]amino}ethyl) hexanoic acid with an optical purity of 99.75%, as measured by chiral HPLC.

Example 3

Preparation of (3S)-5-methyl-3-(2-oxo-2{[(1S)-1-phenylethyl]amino}ethyl) hexanoic acid compound (24)

A three-necked flask equipped with an addition funnel, thermometer pocket, drying tube and a mechanical stirrer, was charged with toluene (1000 ml), (S)-(–)-phenylethylamine (266.9 g, 2.206 mole), and 4-dimethylaminopyridine (1.79 g, 0.0147 mole). The mixture was cooled to a temperature of –40° C. to –50° C., followed by addition of a solution of 3-isobutyl glutaric anhydride (250 g, 1.471 mole) in toluene (250 ml), over a period of 45-60 minutes, and stirring for additional 1.5-2 hours, at a temperature of –40° C. to –50° C. The mixture was then extracted with 3.5-4.0% aqueous solution of NaOH (2350 ml), and the aqueous phase was washed with toluene (1×250 ml). The pH of the aqueous phase was adjusted to 2-2.5 by adding a solution of hydrochloric acid (1-12N). The aqueous phase was further extracted with ethyl acetate (1×1250 ml and 1×500 ml), followed by drying the combined ethyl acetates extracts over anhydrous sodium sulphate, and stripping off the solvents to obtain a residue. The residue was crystallized from toluene to get 344 g (80.5% yield) of a white solid of (3S)-5-methyl-3-(2-oxo-2-{[(1S)-1-phenylethyl]amino}ethyl) hexanoic acid with an optical purity of 98.69%, as measured by chiral HPLC.

Example 4

Preparation of (R)-3-isobutylpentanedioic acid amide-((S)-1-phenylethyl)amide (25)

A three-necked flask equipped with an addition funnel, thermometer pocket, drying tube and a mechanical stirrer, was charged with methylene dichloride (1000 ml), (3S)-5-methyl-3-(2-oxo-2{[(1S)-1-phenylethyl]amino}ethyl) hexanoic acid compound (24) (200 g, 0.687 mole), and with triethylamine (7.65 g, 0.756 mole), and cooled to 0°-5° C. followed by addition of ethyl chloroformate (90 g, 0.825 mole). The mixture was stirred for 1-2 hours at a temperature of 20° C. to 25° C., followed by quenching with 25% aqueous ammonia (1000 ml). The resulted slurry was filtered and washed with water and dried to get 140 g (70.0% yield) of a white solid of (R)-3-isobutylpentanedioic acid amide-((S)-1-phenylethyl)amide of formula 25A, with a purity of 95%, as measured by HPLC.

Example 5

Preparation of (R)-3-isobutylpentanedioic acid amide-((S)-1-phenylethyl)amide (25)

A three-necked flask equipped with an addition funnel, thermometer pocket, drying tube and a mechanical stirrer, was charged with methylene dichloride (500 ml), (3S)-5-methyl-3-(2-oxo-2{[(1S)-1-phenylethyl]amino}ethyl)hexanoic acid compound (24) (100 g, 0.343 mole), and with triethylamine (41.67 g, 0.412 mole), and cooled to –15° C. to –20° C. followed by addition of ethyl chloroformate (39.1 g, 0.36 mole). The mixture was stirred for 1-2 hours at a temperature of –15° C. to –20° C., followed by quenching over a solution of 20% aqueous ammonia (280 ml). The dichloromethane was distilled out from the mass followed by filtering the resulted slurry, washed with water and dried to get 87 g (87% yield) of a white solid of (R)-3-isobutylpentanedioic acid amide-((S)-1-phenylethyl)amide of formula 25A, with a purity of 98%, as measured by HPLC.

Example 6

Preparation of (R)-3-isobutylpentanedioic acid amide-((S)-1-phenylethyl) amide (25)

A three-necked flask equipped with an addition funnel, thermometer pocket, drying tube and a mechanical stirrer, was charged with methylene dichloride (125 ml), (3S)-5-methyl-3-(2-oxo-2{[(1S)-1-phenylethyl]amino}ethyl) hexanoic acid compound (24) (25 g, 0.086 mole), triethyl amine (10.43 g, 0.129 mole), and cooled to 0°-5° C. followed by addition of pivaloyl chloride (12.43 g, 0.103 mole). The mixture was stirred for 1-2 hours at a temperature of 20° C. to 25° C., followed by quenching with 20% aqueous ammonia (250 ml). The resulted slurry was filtered and washed with water and dried to get 15.2 g (61% yield) of a white solid of (R)-3-isobutylpentanedioic acid amide-((S)-1-phenylethyl)amide of formula 25A, with a purity of 95%, as measured by HPLC.

Example 7

Preparation of (R)-3-isobutylpentanedioic acid amide-((S)-1-phenylethyl) amide (25)

A three-necked flask equipped with an addition funnel, thermometer pocket, drying tube and a mechanical stirrer, was charged with acetone (125 ml), (3S)-5-methyl-3-(2-oxo-2{[(1S)-1-phenylethyl]amino}ethyl) hexanoic acid compound (24) (25 g, 0.086 mole), triethyl amine (10.43 g, 0.129 mole), and cooled to 0-5° C. followed by addition of pivaloyl chloride (12.43 g, 0.103 mole). The mixture was stirred for 1-2 hours at a temperature of 20° C. to 25° C., followed by quenching with 20% aqueous ammonia (250 ml). The resulted slurry was filtered and washed with water and dried to get 10.68 g (43.4% yield) of a white solid of (R)-3-isobutylpentanedioic acid amide-((S)-1-phenylethyl)amide of formula 25, with a purity of 95.4%, as measured by HPLC.

Example 8

Preparation of {(S)-4-methyl-2-[((S)-1-phenylethylcarbamoyl)-methyl]pentyl}carbamic acid methyl ester (26)

A three-necked flask equipped with an addition funnel, thermometer pocket, drying tube and a mechanical stirrer, was charged with methanol (1400 ml), and cooled to −40° to −45° C. followed by addition of sodium methoxide (130 g, 2.413 mole). A solution of bromine (154.48 g, 0.965 mole) in methanol (300 ml) was slowly added at about −40 to −45° C. followed by addition of (R)-3-isobutylpentanedioic acid amide-((S)-1-phenylethyl)amide, of formula 25 (140 g, 0.48 mole), in methanol (560 ml). The mixture was gradually warmed to a temperature of 0° C. and then to 55-60° C., followed by stirring for 2 to 3 hours. The solvent was then stripped off and water was added to the mass. The resulted slurry was further extracted with methylene dichloride (1×500 ml and 1×250 ml), followed by drying the combined methylene dichloride extracts over anhydrous sodium sulphate, and stripping off the solvents to obtain a residue. The residue was crystallized from diisopropyl ether to get 115 g (74.2.0% yield) of a white solid of {(S)-4-methyl-2-[((S)-1-phenylethylcarbamoyl)-methyl]pentyl}carbamic acid methyl ester (26) with a purity of 92%, as measured by HPLC.

Example 9

Preparation of {(S)-4-methyl-2-[((S)-1-phenylethylcarbamoyl)-methyl]pentyl}carbamic acid methyl ester (26)

A three-necked flask equipped with an addition funnel, thermometer pocket, drying tube and a mechanical stirrer, was charged with methanol (2000 ml), and cooled to −15° to −20° C., (R)-3-isobutylpentanedioic acid amide-((S)-1-phenylethyl)amide, of formula 25 (100 g, 0.344 mole) followed by addition of sodium methoxide (74.5 g, 1.38 mole). Bromine (82.56 g, 0.516 mole) was slowly added at about −15 to −20° C. The mixture was gradually warmed to a temperature of 0° C. and then to 55-60° C., followed by stirring for 2 to 3 hours. The solvent was then stripped off and water was added to the mass. The resulted slurry was further extracted with methylene dichloride (1×500 ml), followed by washing the methylene dichloride extract with water and brine solution. The solvent was stripped off and the residue was crystallized from a mixture of methylene dichloride and cyclohexane to get 95 g (85.8.0% yield) of a white solid of {(S)-4-methyl-2-[((S)-1-phenylethylcarbamoyl)-methyl]pentyl}carbamic acid methyl ester (26) with a purity of 93%, as measured by HPLC.

Example 10

Preparation of {(S)-2-carbamoylmethyl-4-methylpentyl)carbamic acid methyl ester (27)

A 2 l, four-necked flask, equipped with a mechanical stirrer, thermometer pocket and a liquid ammonia inlet, was charged with {(S)-4-methyl-2-[((S)-1-phenylethylcarbamoyl)-methyl]pentyl}carbamic acid methyl ester (26) (25 g, 0.078 mole), tetrahydrofuran (175 ml), and water (25 ml). The reaction mixture was cooled to −40° to −60° C. and liquid ammonia (1000 ml) was added followed by addition of small pieces of sodium metal (7.2 g). The resultant reaction mixture was stirred vigorously for 4-10 hours until the ammonia had evaporated. Water (100 ml) was added to the reaction mass under $N_2$ atmosphere at 5°-10° C., followed by separating the phases. The organic layer was separated and dried over anhydrous sodium sulphate and the solvent was stripped off The residue was crystallized from diisopropyl ether to get 10.2 g (60% yield) of {(S)-2-carbamoylmethyl-4-methylpentyl)carbamic acid methyl ester with purity of 73% as measured by HPLC.

Example 11

Regeneration of 3-isobutylglutaric acid

A 3 l four-necked flask, equipped with a mechanical stirrer, thermometer pocket, and condenser, was charged with a residue after crystallization of compound 24A, (250 g) from examples 1 and 2, and 70% sulfuric acid (2500 g). The reaction mixture was refluxed at 115°-125° C. for 5-10 hours, and then cooled to 20°-25° C. and diluted with water. The aqueous layer was extracted with toluene (1×1000 ml and 1×500 ml). The combined organic phase was extracted with 5% sodium hydroxide solution (1500 ml), and the pH of the aqueous layer was adjusted to 1.5-2 with concentrated hydrochloric acid, followed by extractions with toluene (1×600 ml and 1×400 ml). The combined organic layers were dried over anhydrous sodium sulphate and the solvent was stripped off to obtain 3-isobutyl glutaric acid (128 g) in purity of 94% as measured by GC.

3-isobutylglutaric acid is characterized by:
1. IR (KBr): 1713.27 $cm^{-1}$.
2. $^1$H NMR (CDC13): δ0.89-0.92 (d, 6H), 1.25 (t, 2H), 1.6-1.69 (septet, 1H), 2.42 (s, 4H), 11.96 (s, 2H).
3. $^{13}$C NMR (CDCl$_3$): δ22.39, 25.06, 28.11, 29.50, 38.45, 43.38, 179.17, 203.

Example 12

Converting 3-isobutylglutaric acid to 3-isobutylglutaric anhydride, compound 22

A 1 l, four-necked flask equipped with a mechanical stirrer, thermometer pocket and condenser, was charged with 3-isobutyl glutaric acid (500 g) and acetic anhydride (326 g). The reaction mixture was refluxed at 135°-1450° C. for 2.5-3 hours, followed by distilling out the unreacted acetic anhydride at 147°-155° C., and then the distillation was continued under vacuum to ensure removal of traces of unreacted acetic anhydride. The residue was cooled to 25°-30° C. to obtain 445 g of 3-isobutylglutaric anhydride.

Example 13

Preparation of (S)-Pregabalin

A 0.2 l reactor was loaded with 6N hydrochloric acid (100 ml) containing compound 27 (12 g, 0.055 mole), and was heated to 100°-110° C. for 12-24 hours, and then cooled to room temperature, i.e., about 20° to about 25° C. An aqueous 40% sodium hydroxide solution was added in an amount sufficient to provide a pH of 1. The solution was then extracted with 37 ml of iso-butanol, the organic layer was separated, and Bu$_3$N was added in an amount sufficient to provide a pH of 4. The (S)-Pregabalin was precipitated, filtered, and washed with 10 ml of iso-butanol. After drying at 55° C. under vacuum, (S)-Pregabalin was obtained as white crystals in a 21.5% yield. Purity: 99.9% area by HPLC.

Example 14

Preparation of (S)-Pregabalin

A 0.2 l reactor was loaded with 70% sulfuric acid (200 g) containing compound 26 (10 g, 0.031 mole), and was heated to 115-120° C. for 5-10 hours, and then cooled to room temperature, i.e., about 20° to about 25° C. An aqueous 40% sodium hydroxide solution was added in an amount sufficient to provide a pH of 1. The solution was then extracted with 35 ml of iso-butanol, the organic layer was separated, and Bu₃N was added in an amount sufficient to provide a pH of 4. The (S)-Pregabalin was precipitated, filtered, and washed with 10 ml of iso-butanol. After drying at 55° C. under vacuum, (S)-Pregabalin was obtained as white crystals in a 40.4% yield. Purity: 99.95% area by HPLC.

Example 15

Preparation of (S)-Pregabalin

A 0.2 l reactor was loaded with 70% sulfuric acid (200 g) containing compound 26 (10 g, 0.031 mole), and was heated to 115-120° C. for 5-10 hours, and then cooled to room temperature, i.e., about 20° to about 25° C. An aqueous 40% sodium hydroxide solution was added in an amount sufficient to provide a pH of 1. The solution was then extracted with 50 ml of isopropanol, the organic layer was separated, and NH₄OH was added in an amount sufficient to provide a pH of 4. The (S)-Pregabalin was precipitated, filtered, and washed with 10 ml of isobutanol. After drying at 55° C. under vacuum, (S)-Pregabalin was obtained as white crystals in a 50.4% yield. Purity: 99.05% area by HPLC.

Example 16

Preparation of (S)-Pregabalin

A flask was loaded with 47% HBr (12 ml), water (6 ml), and compound 26 (6 g), and then was heated to reflux for 3 hours. The solution was cooled to room temperature, and water (12 ml) was added. An aqueous 47% sodium hydroxide solution was added to obtain pH of 3. The solution was then extracted twice with isobutanol (15 ml), the combined organic layers were evaporated and fresh isobutanol was added (15 ml). Bu₃N (3.8 g) was added. The mixture was cooled to 2° C. for 1 hour, then (S)-Pregabalin was filtered, and washed with of iso-butanol (3 ml). After drying at 55° C. under vacuum, (S)-Pregabalin was obtained as white crystals in a 90% yield.

Example 17

Preparation of (S)-Pregabalin

A flask was loaded with 47% HBr (30 ml), water (15 ml), and compound 26 (15 g), and then was heated to reflux for 3 hours. The solution was cooled to room temperature and water (30 ml) was added. An aqueous 47% sodium hydroxide solution was added to obtain pH of 3. The solution was then extracted twice with iso-butanol (37.5 ml). The organic layers were combined and Bu₃N (9.5 g) was added. The mixture was cooled to 2° C. for 1 hour, then (S)-Pregabalin was filtered, and washed with of iso-butanol (10 ml). After drying at 55° C. under vacuum, (S)-Pregabalin was obtained as white crystals in a 51% yield.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

We claim:

1. A process for preparing (S)-Pregabalin:

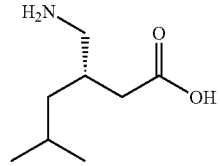

comprising:

a) preparing a compound of the following formula 24:

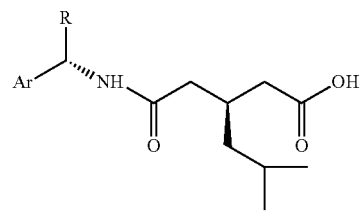

wherein Ar is a $C_{6-10}$ aromatic group and R is a straight or branched $C_{1-4}$ alkyl, ester, or carboxylic acid;

b) reacting the compound of formula 24 with an amidation reagent to produce a compound of the following formula 25:

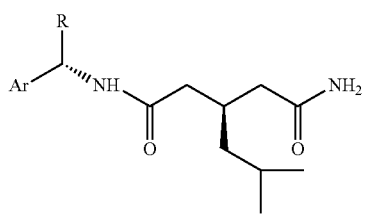

wherein Ar is a $C_{6-10}$ aromatic group, and R is a straight or branched $C_{1-4}$ alkyl, ester, or carboxylic acid;

c) carrying out a Hoffman reaction on the compound of formula 25 to produce a compound of the following formula 26:

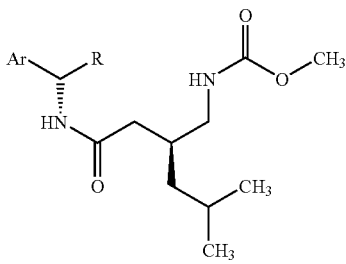

wherein Ar is a $C_{6-10}$ aromatic group, and R is a straight or branched $C_{1-4}$ alkyl, ester, or carboxylic acid;

d) reacting the compound of formula 26 with ammonia and an alkali metal to produce a compound of the following formula 27;

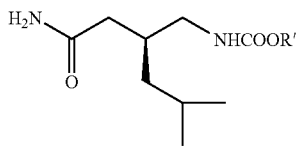

wherein R' is a straight or branched $C_{1-5}$ alkyl; and e) reacting the compound of formula 27 with an acid to produce (S)-Pregabalin.

2. The process according to claim 1, wherein the compound of formula 24 is prepared by a process comprising:

a1) combining a chiral amine of the following formula 23,

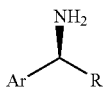

wherein Ar is a $C_{6-10}$ aromatic group, and R is a straight or branched $C_{1-4}$ alkyl, ester, or carboxylic acid, an organic solvent selected from at least one of $C_{6-10}$ aromatic hydrocarbons, substituted aromatic hydrocarbons, $C_{2-8}$ ethers, halogenated hydrocarbons, straight or branched $C_{1-4}$ alcohols, $C_{3-4}$ esters, straight, branched or cyclic $C_{1-6}$ alkanes, or $C_{3-8}$ ketones, and at least one base, to obtain a mixture;

b1) cooling the mixture to a temperature of about $-70°$ C. to about $10°$ C.;

c1) adding 3-isobutyl glutaric anhydride to the mixture;

d1) maintaining the mixture at a temperature of about $-70°$ C. to about $10°$ C. for at least about one hour to obtain the compound of formula 24; and e1) recovering the compound of formula 24 from the mixture.

3. The process according to claim 2, wherein the chiral amine of formula 23 is methylbenzylamine.

4. The process according to claim 2, wherein the chiral amine of formula 23 is (S)-methylbenzylamine.

5. The process according to claim 2, wherein the organic solvent is at least one of toluene, tert-butyl methyl ether, tetrahydrofuran, diisopropyl ether, diethyl ether, dichloromethane, isopropyl alcohol, ethanol, methanol, n-butanol, ethyl acetate, isopropyl acetate, isobutyl acetate, hexane, cyclohexane, acetone, methyl isobutyl ketone, and methyl ethyl ketone.

6. The process according to claim 2, wherein the organic solvent is toluene.

7. The process according to claim 2, wherein the base is an organic base.

8. The process according to claim 2, wherein the base is diethyl amine, triethyl amine, di-n-propyl amine, di-isopropyl amine, tertbutylamine, morpholine, piperidine, pyridine, or 4-dimethyl aminopyridine.

9. The process according to claim 2, wherein the base is 4-dimethyl aminopyridine.

10. The process according to claim 2, wherein the mixture is maintained at a temperature of about $0°$ C. to about $-50°$ C.

11. The process according to claim 2, wherein the mixture is maintained at a temperature of about $-40°$ C. to $-30°$ C.

12. The process according to claim 2, wherein the mixture is maintained for about one hour to about six hours.

13. The process according to claim 2, wherein the mixture is maintained for about one hour to about two hours.

14. The process according to claim 2, further comprising crystallizing the recovered compound of formula 24 obtained in step e1) from a second organic solvent.

15. The process according to claim 14, wherein the second organic solvent is selected from the group consisting of esters, nitriles, ethers, $C_{4-6}$ straight, branched or cyclic hydrocarbons, and $C_{6-10}$ substituted aromatic hydrocarbons.

16. The process according to claim 14, wherein the organic solvent is ethyl acetate, acetonitrile, methyl t-butyl ether, toluene, xylene, hexane, or cyclohexane.

17. The process according to claim 14, wherein the organic solvent is a mixture of toluene and ethyl acetate.

18. The process according to claim 2, wherein the compound of formula 24 is recovered in an optical purity of at least about 93% area by HPLC.

19. The process according to claim 2, wherein the compound of formula 24 is recovered in an optical purity of about 98% to about 100% area by HPLC.

20. The process according to claim 2, wherein the compound of formula 24 is recovered in an optical purity of about 99% to about 100% area by HPLC.

21. The process according to claim 1, wherein the compound of formula 24 is converted into the compound of formula 25 by a process comprising:

a1) combining at a temperature of about $20°$ C. to about $-30°$ C., the compound of formula 24 and at least one organic solvent selected from the group consisting of substituted aromatic hydrocarbons, $C_{6-10}$ aliphatic hydrocarbons, halogenated hydrocarbons, ethers and ketones, an amidation reagent selected from the group consisting of $C_{1-4}$ alkyl and $C_{6-8}$ aryl haloformates, and acid halides, and a base to form a mixture;

b1) maintaining the mixture for about one hour to about two hours at a temperature of about $-10°$ C. to about $20°$ C.;

c1) adding ammonia to obtain the compound of formula 25; and d1) recovering the compound of formula 25 from the mixture.

22. The process according to claim 21, wherein the ammonia is provided in an aqueous solution.

23. The process according to claim 21, wherein the amidation reagent is an ethyl or methyl derivative of a chloro or bromoformate, a benzyl chloro or bromoformate, or an acetyl, pivaloyl, oxaloyl or benzoyl chloride or bromide.

24. The process according to claim 21, wherein the amidation reagent is ethylchloroformate, methylchloroformate, or an acetyl, pivaloyl, oxaloyl or benzoyl chloride.

25. The process according to claim 21, wherein the amidation reagent is ethyl-chloroformate or methylchloroformate.

26. The process according to claim 21, wherein the organic solvent is toluene, xylene, hexane, heptane, acetone, methyl ethyl ketone, methyl isobutyl ketone, diethyl ether, diisopropyl ether, tert-butyl methyl ether, or dichloromethane.

27. The process according to claim 21, wherein the organic solvent is acetone or dichloromethane.

28. The process according to claim 21, wherein the base is an organic base.

29. The process according to claim 21, wherein the base is diethyl amine, triethyl amine, di-n-propyl amine, di-isopropyl amine, tri-n-butyl amine, morpholine, piperidine, pyridine, or 4-dimethyl aminopyridine.

30. The process according to claim 21, wherein the base is 4-dimethyl amino-pyridine or triethylamine.

31. The process according to claim 21, wherein the combining step is performed at a temperature of −10° C. to about −20° C.

32. The process according to claim 21, wherein the compound of formula 25 is recovered in a purity of at least about 95% area by HPLC.

* * * * *